United States Patent
Tardif et al.

[19]

[11] Patent Number: 6,070,269
[45] Date of Patent: Jun. 6, 2000

[54] DATA-SUIT FOR REAL-TIME COMPUTER ANIMATION AND VIRTUAL REALITY APPLICATIONS

[75] Inventors: Hervé Fernand Marcel Tardif, Port Haliguen; Pierre Haddad, Paris, both of France

[73] Assignee: Medialab Services S.A., France

[21] Appl. No.: 08/900,104

[22] Filed: Jul. 25, 1997

[51] Int. Cl.[7] .................................................. A41D 1/00
[52] U.S. Cl. .................................. 2/69; 2/912; 600/388; 345/474
[58] Field of Search .......................... 2/243.1, 244, 161.1, 2/69, 912, 913, 914, 917, 919; 345/473, 474, 475; 600/595, 388, 394, 390, 391, 382, 384, 386; 901/46

[56] References Cited

U.S. PATENT DOCUMENTS

| | | | |
|---|---|---|---|
| 4,122,843 | 10/1978 | Zdrojkowski | 600/390 X |
| 4,542,291 | 9/1985 | Zimmerman | 250/231 |
| 4,815,964 | 3/1989 | Cohen et al. | 600/394 |
| 4,937,444 | 6/1990 | Zimmerman | 250/231.1 |
| 4,988,981 | 1/1991 | Zimmerman et al. | 340/709 |
| 5,029,997 | 7/1991 | Faroudja | 352/54 |
| 5,086,785 | 2/1992 | Gentile et al. | 128/782 |
| 5,097,252 | 3/1992 | Harvill et al. | 340/540 |
| 5,136,726 | 8/1992 | Kellin et al. | 2/244 |
| 5,166,463 | 11/1992 | Weber | 84/600 |
| 5,184,815 | 2/1993 | Maddox | 2/161.1 X |
| 5,196,240 | 3/1993 | Stockwell | 427/389.9 |
| 5,255,211 | 10/1993 | Redmond | 364/578 |
| 5,319,387 | 6/1994 | Yoshikawa | 345/179 |
| 5,320,538 | 6/1994 | Baum | 434/307 |
| 5,375,610 | 12/1994 | LaCourse et al. | 128/782 |
| 5,429,140 | 7/1995 | Burdea et al. | 128/774 |
| 5,495,568 | 2/1996 | Beavin | 395/161 |
| 5,495,576 | 2/1996 | Ritchey | 395/125 |
| 5,513,130 | 4/1996 | Redmond | 364/578 |
| 5,526,022 | 6/1996 | Donohue et al. | 345/156 |
| 5,554,033 | 9/1996 | Bizzi et al. | 434/247 |
| 5,610,528 | 3/1997 | Neely et al. | 324/660 |

FOREIGN PATENT DOCUMENTS 0 712 097 A2   7/1995   European Pat. Off. ........ G06T 15/70

*Primary Examiner*—Peter Nerbun
*Attorney, Agent, or Firm*—Coudert Brothers

[57] ABSTRACT

Data-suits for real-time computer animation of cartoon and virtual-reality characters are disclosed. The data-suit have a number of sensors providing time-varying positional data from a human actor.

22 Claims, 13 Drawing Sheets

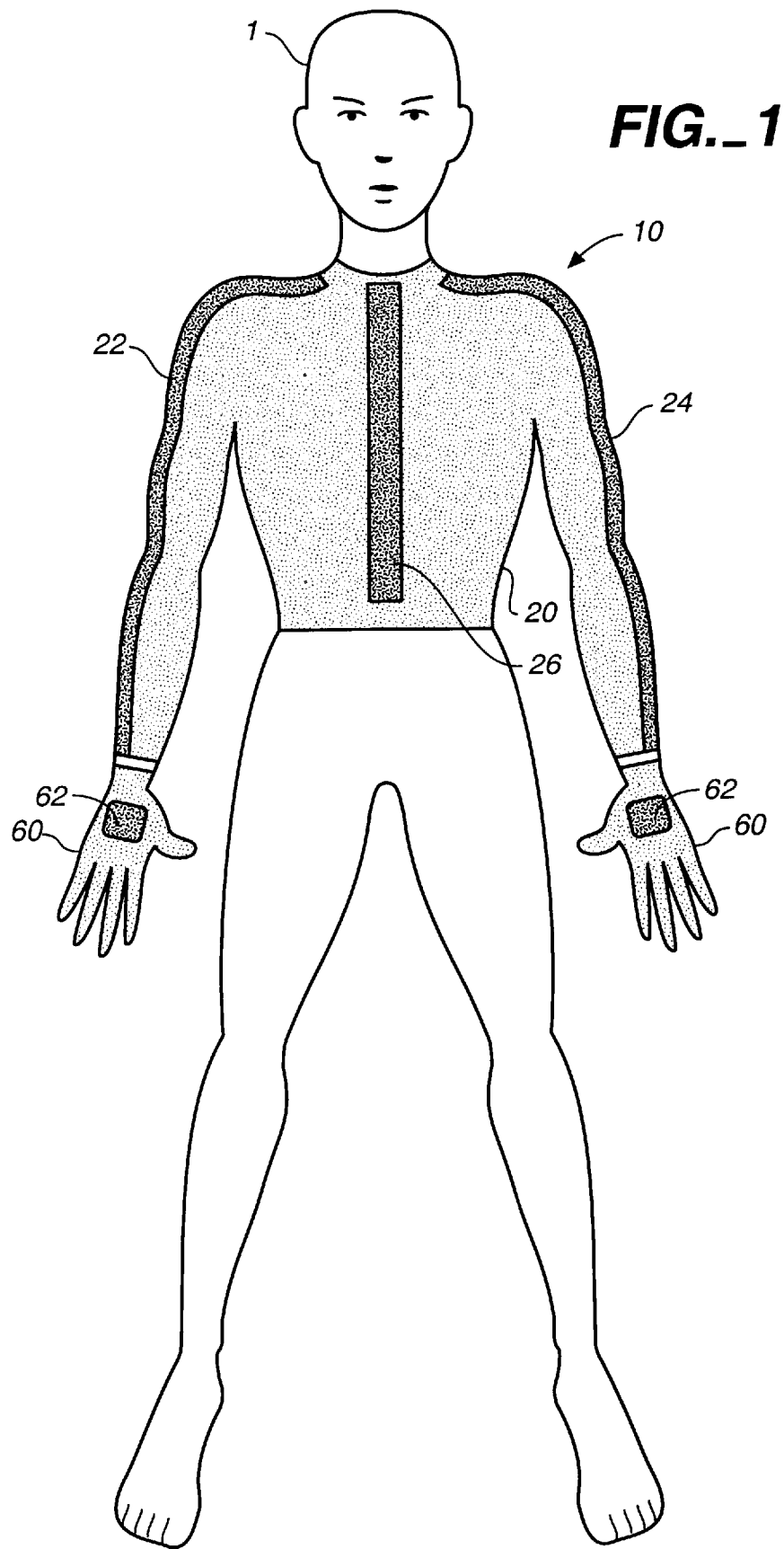
FIG._1

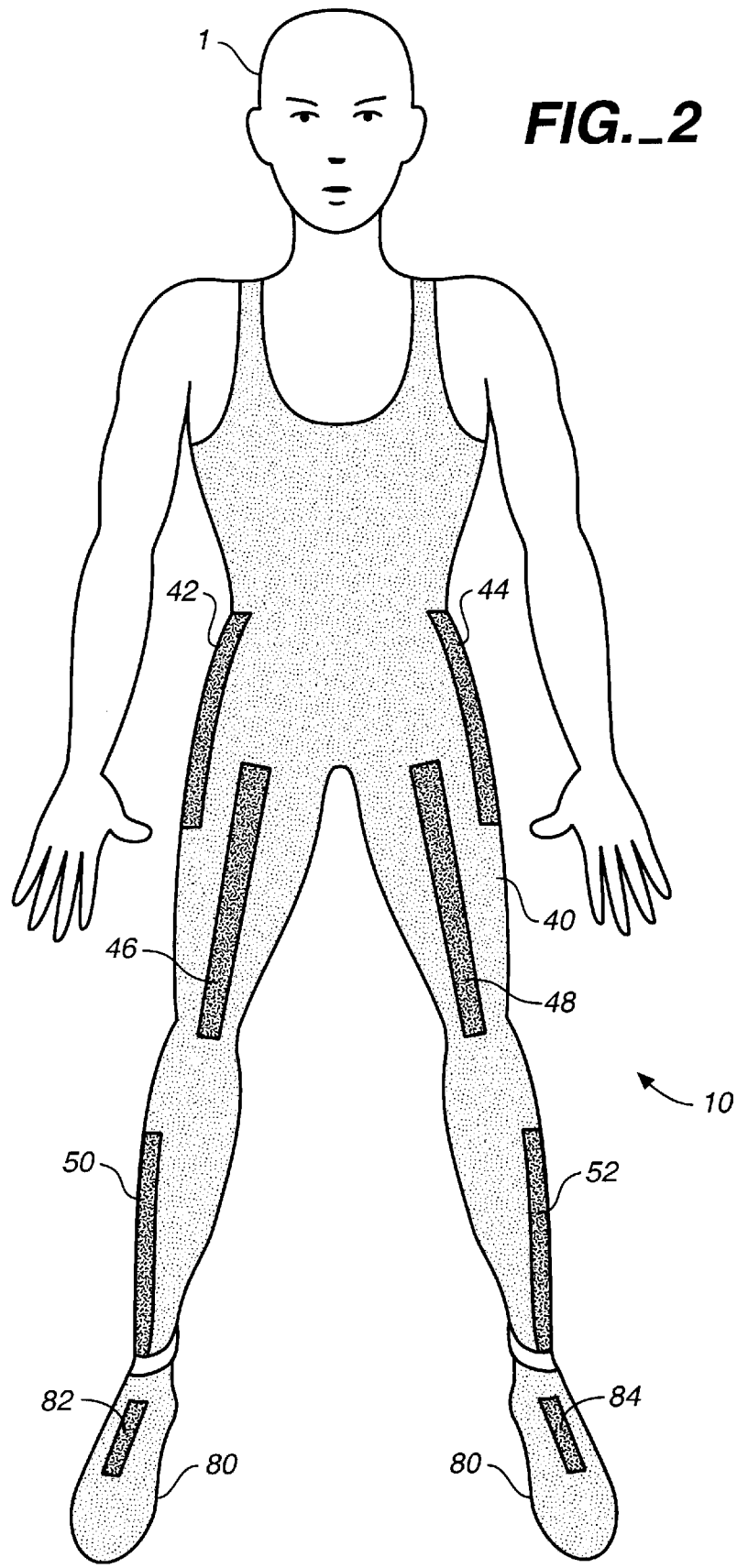
FIG._2

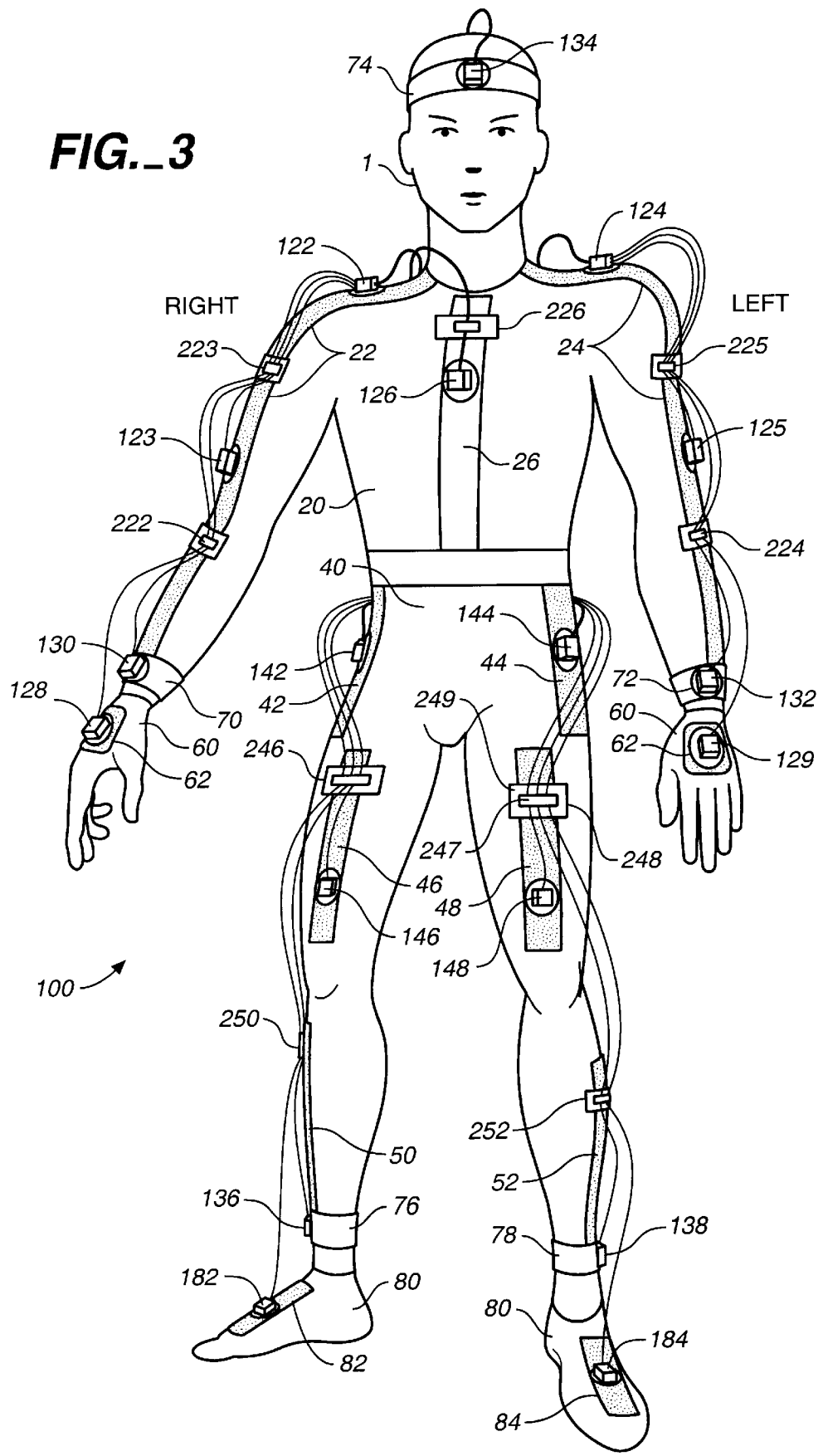

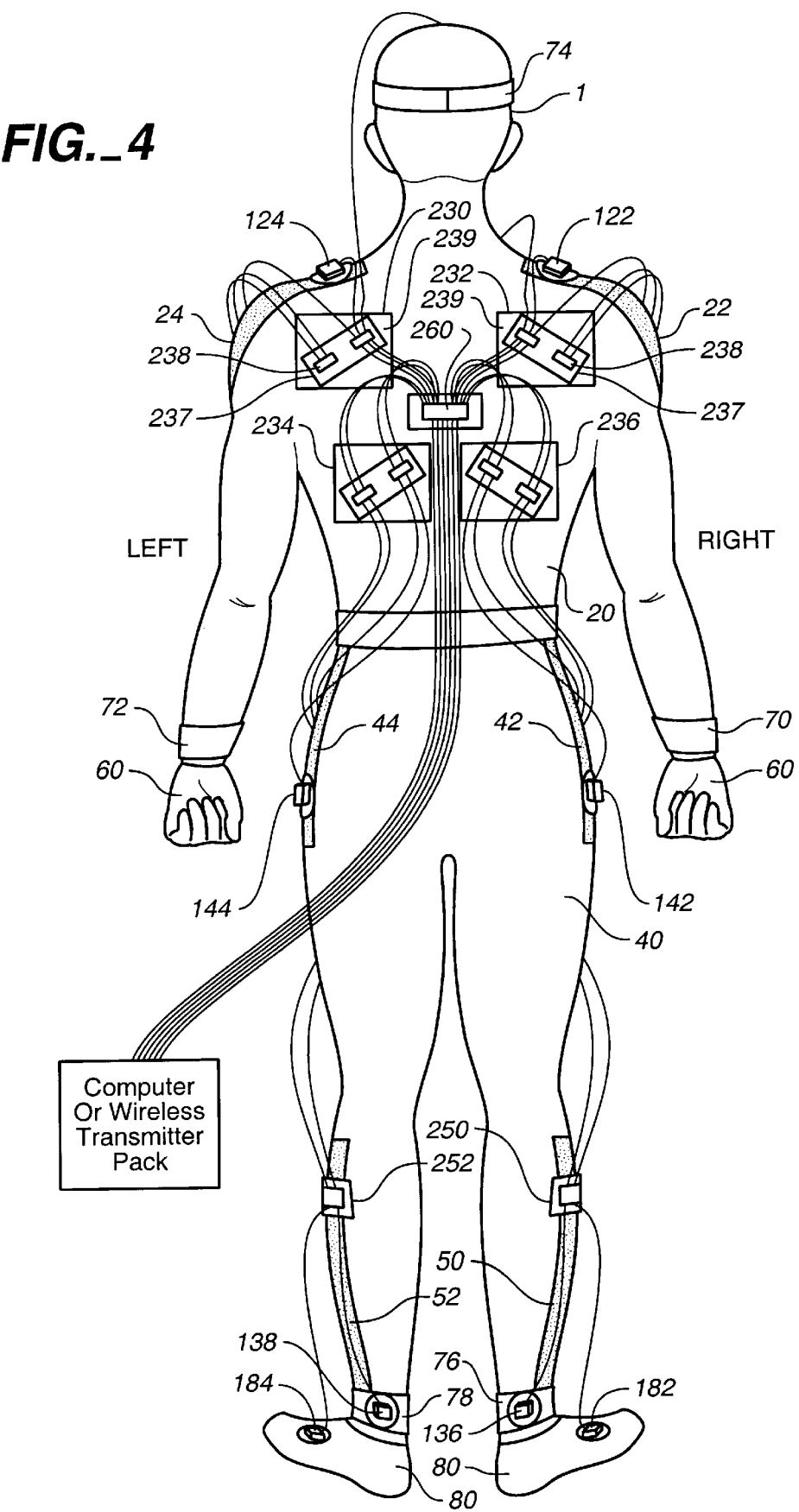
FIG._4

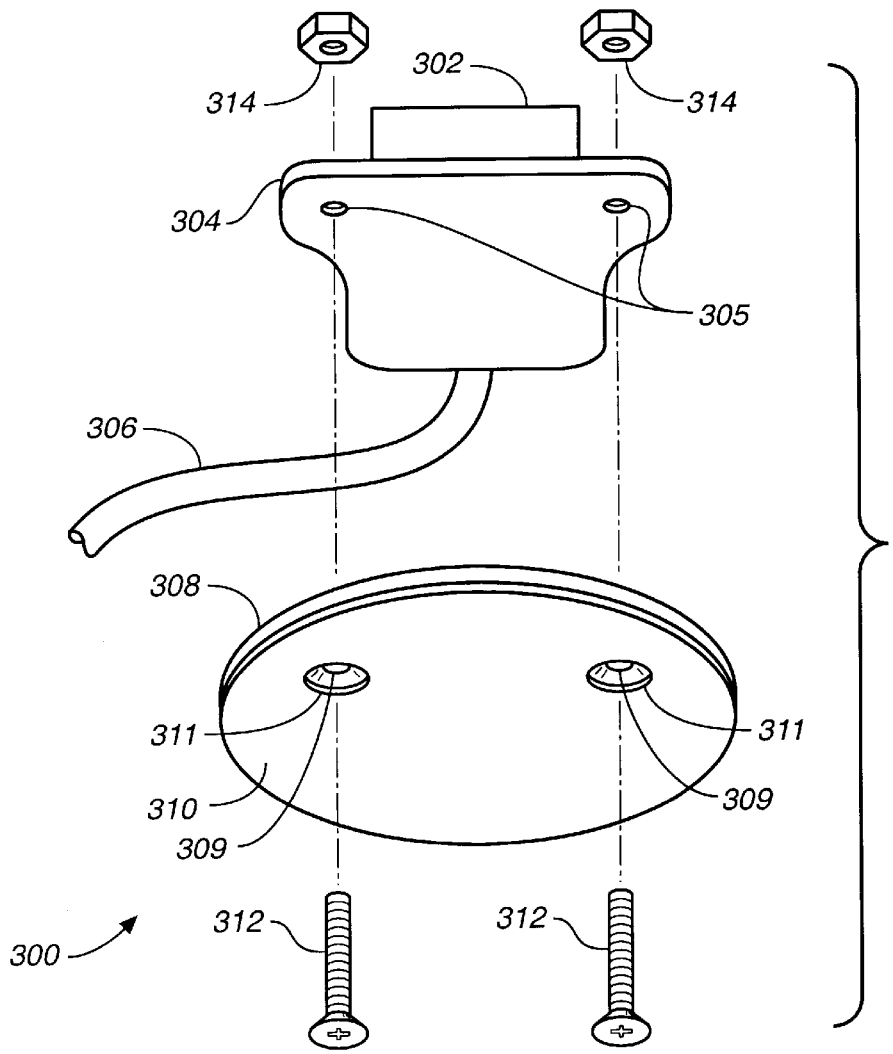
FIG._5
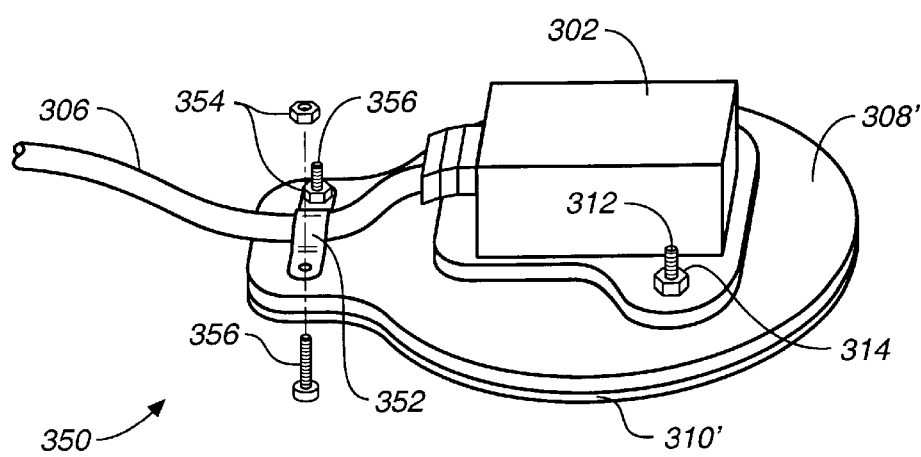
FIG._6

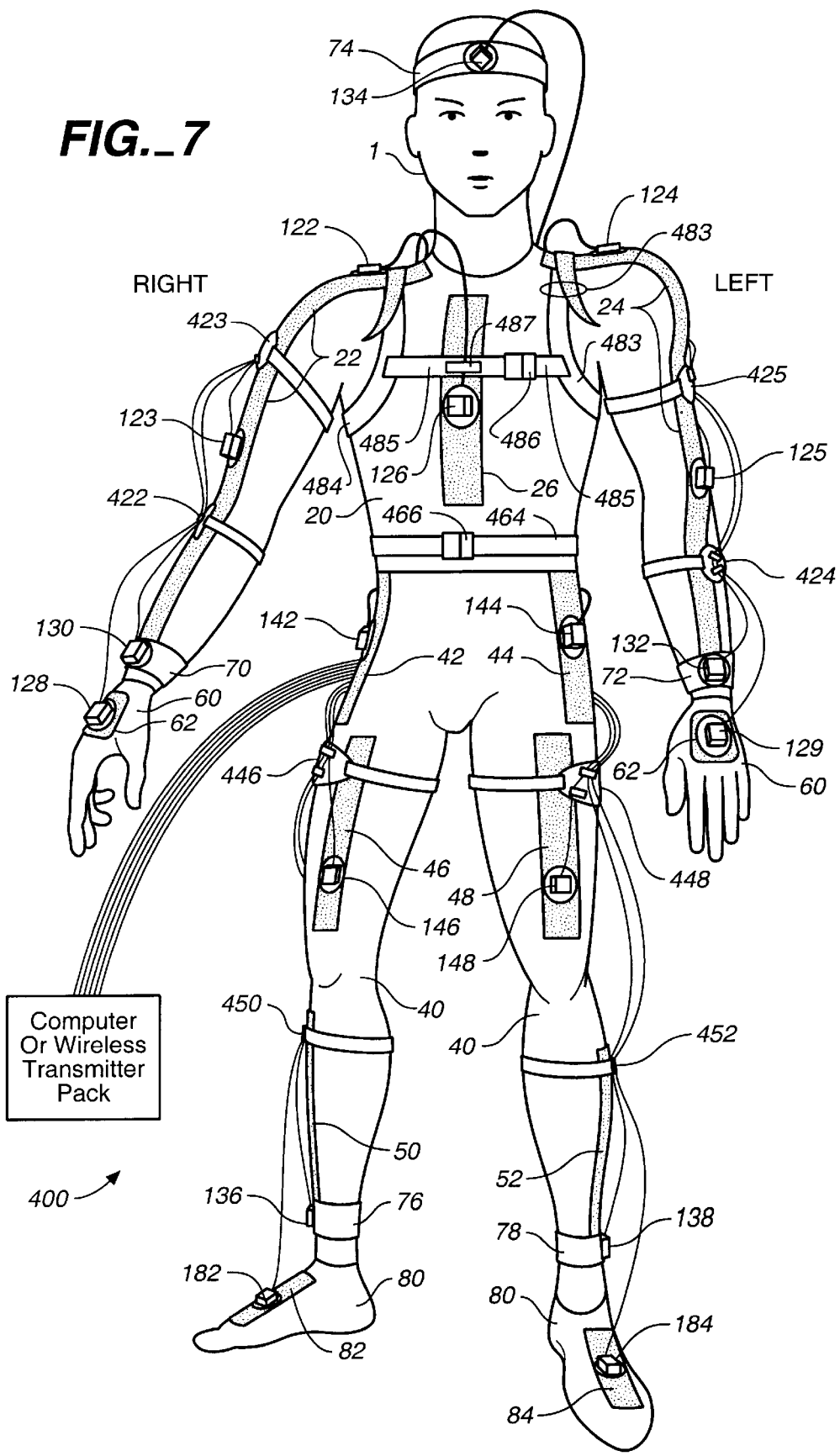
FIG._7

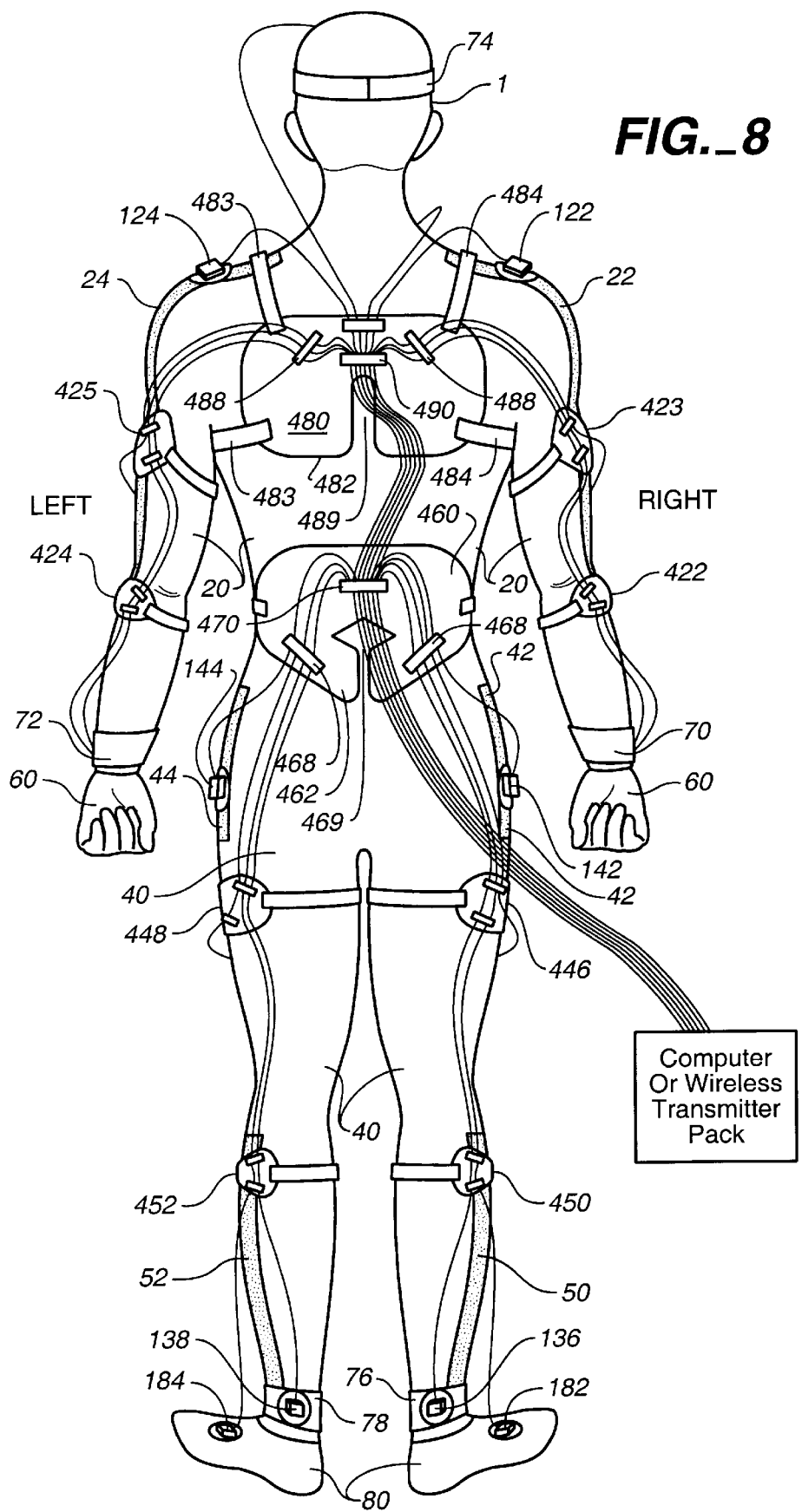
FIG._8

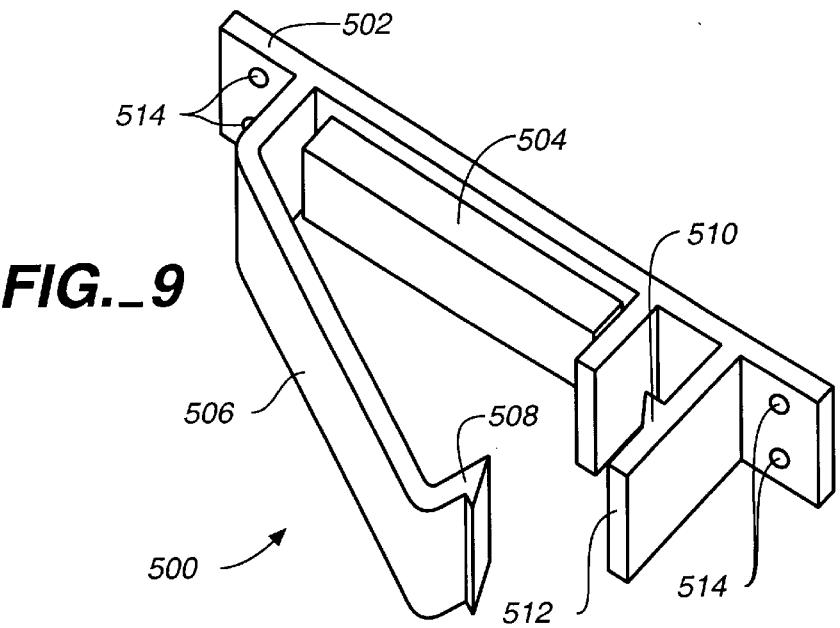
FIG._9
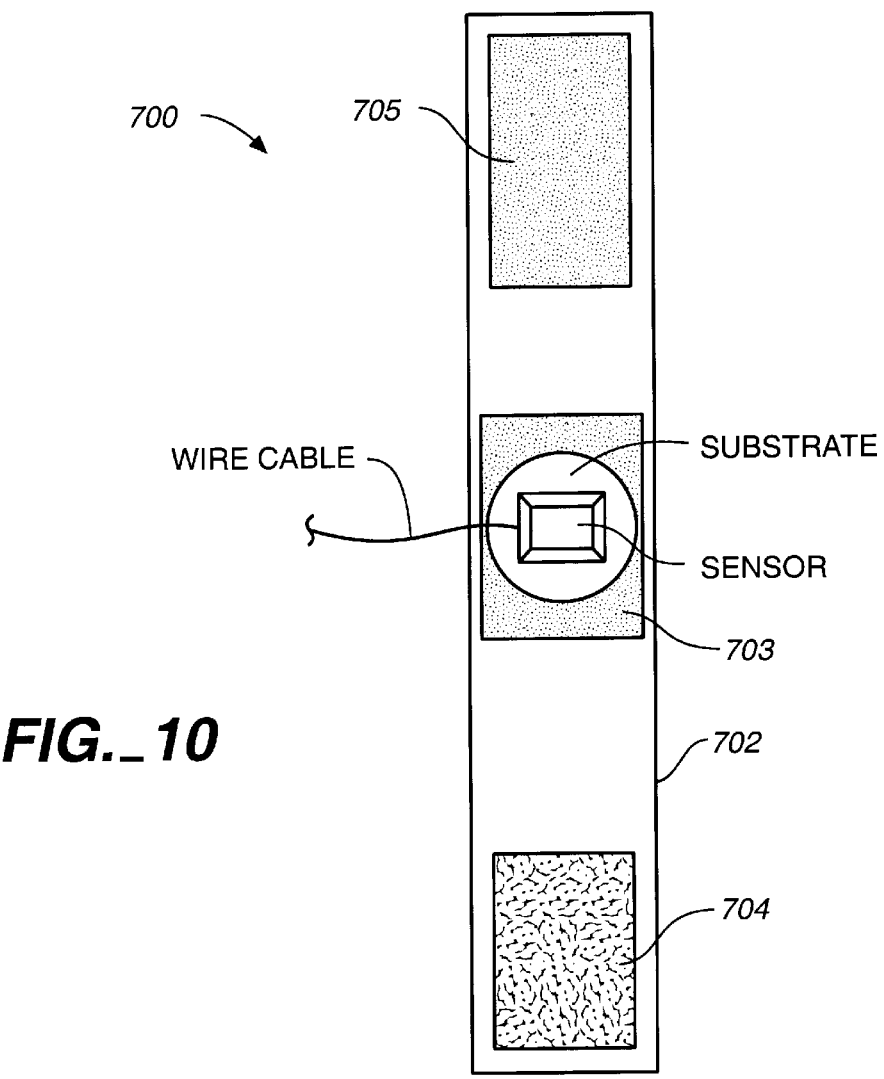
FIG._10

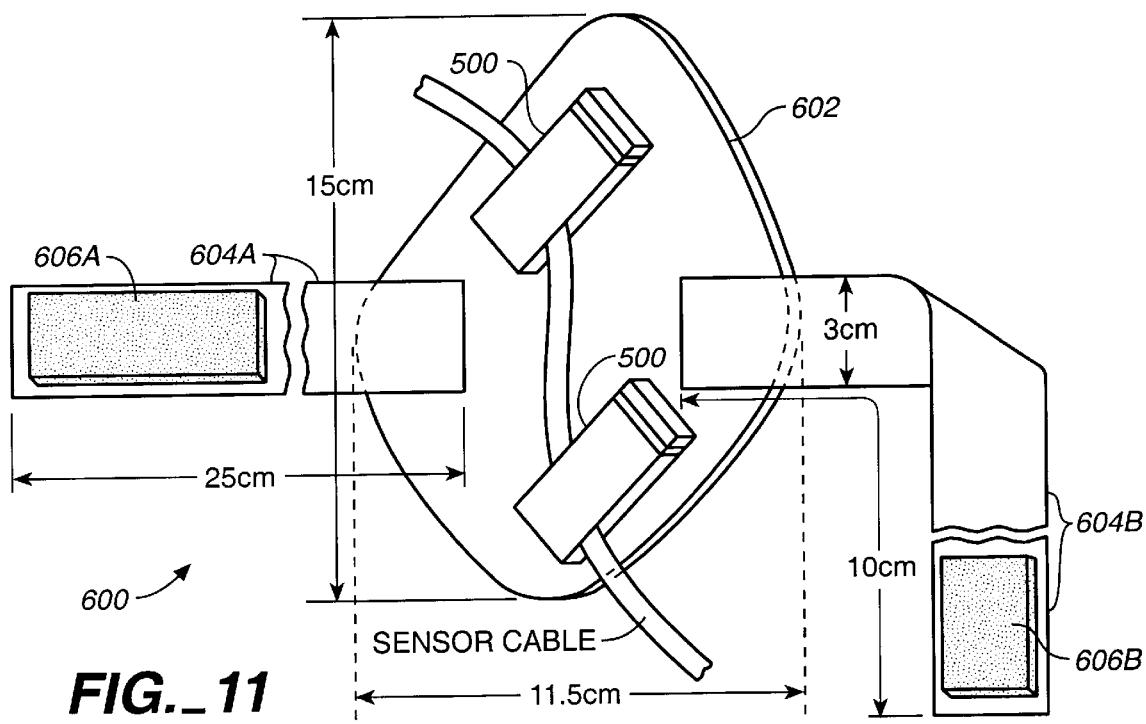
FIG._11
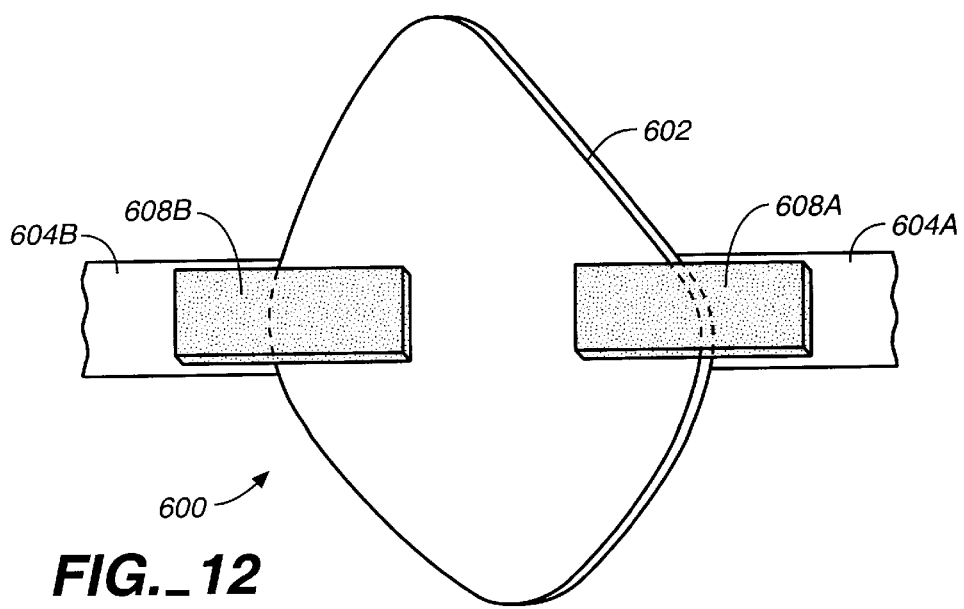
FIG._12

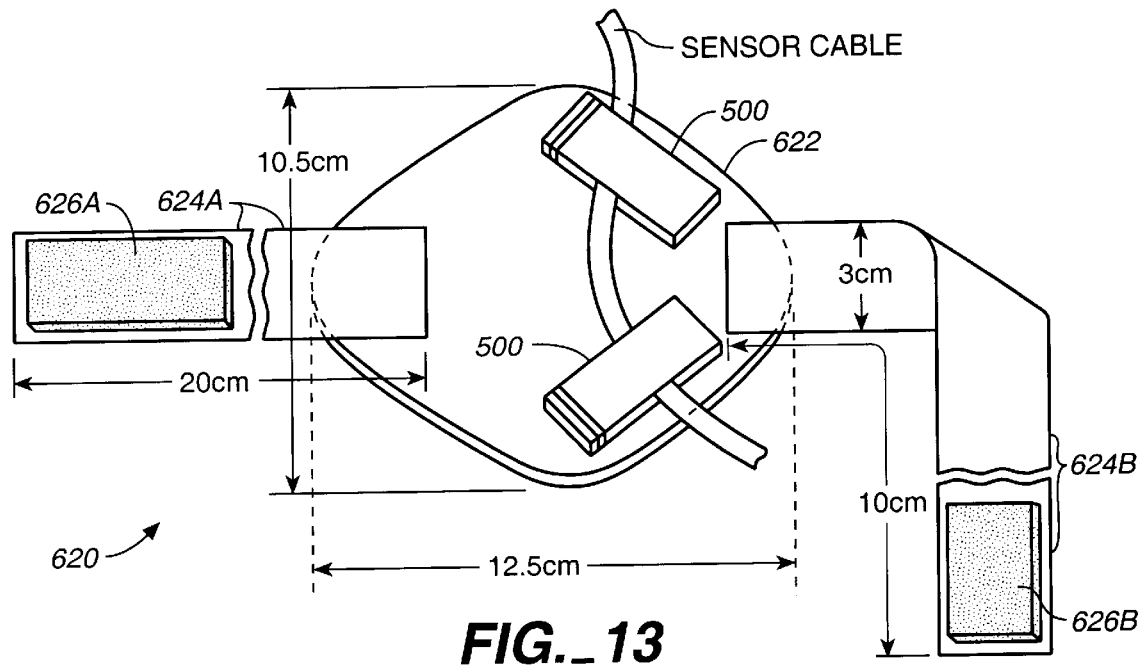
FIG._13
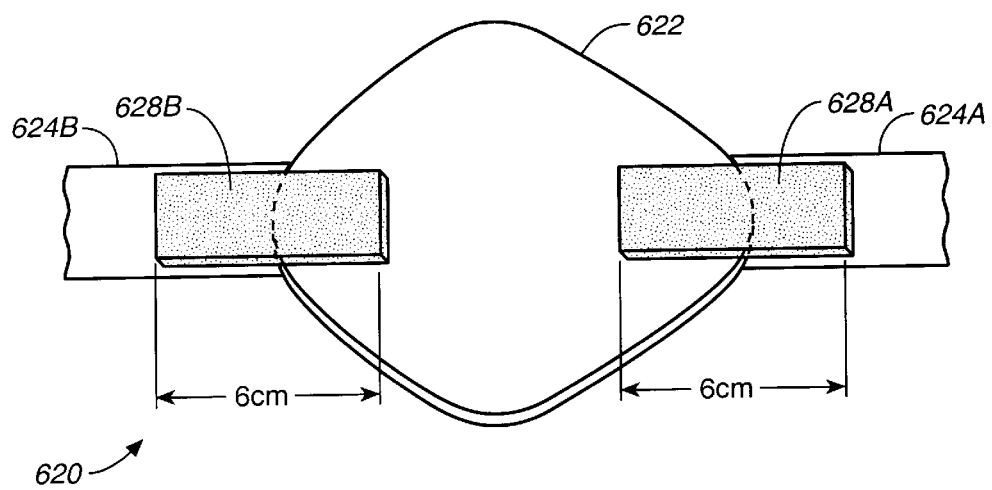
FIG._14

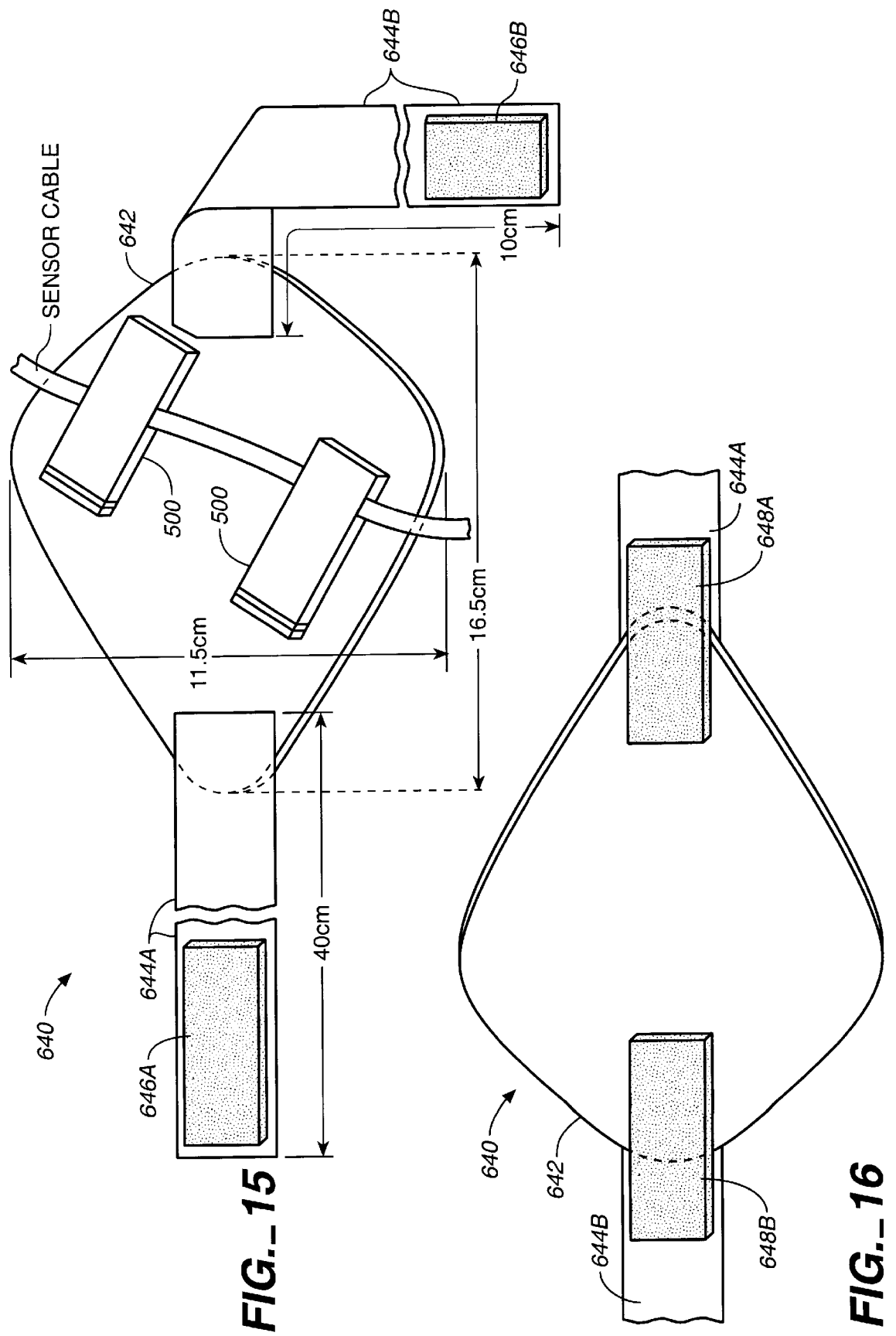

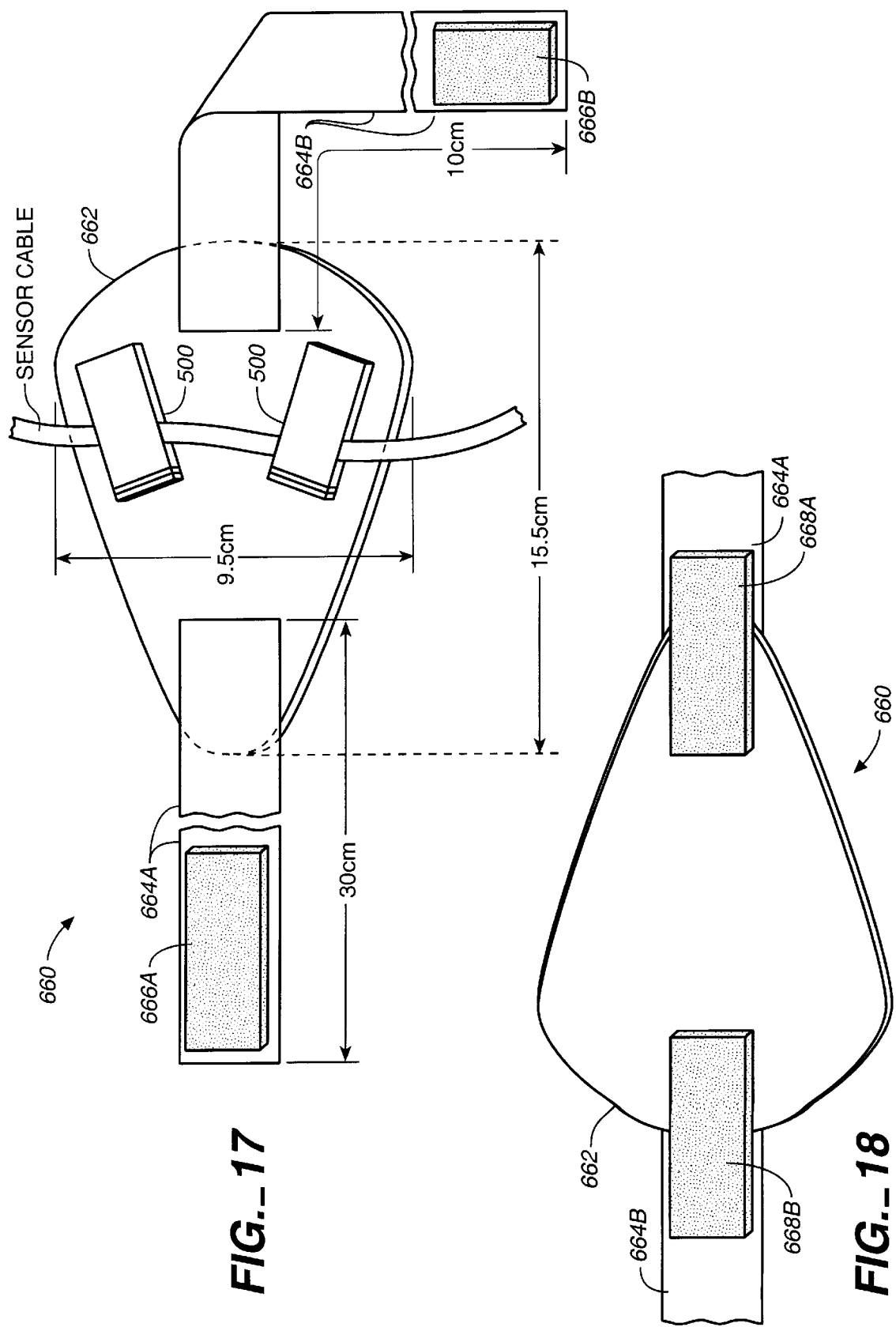

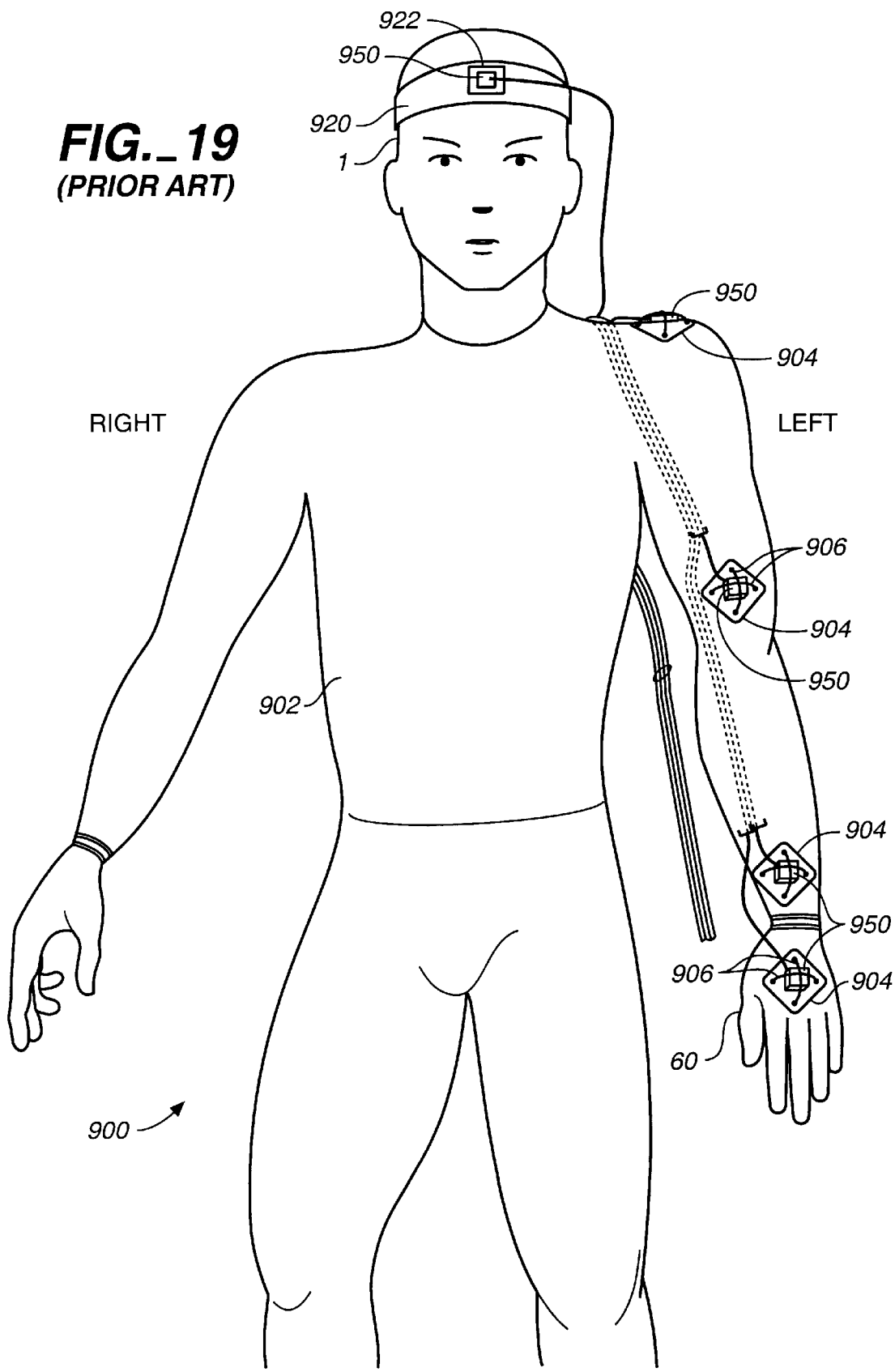
FIG._19 (PRIOR ART)

DATA-SUIT FOR REAL-TIME COMPUTER ANIMATION AND VIRTUAL REALITY APPLICATIONS

FIELD OF THE INVENTION

The present invention relates to real-time computer animation of cartoon and virtual-reality characters using time-varying positional data from a human actor, and more specifically to a data-suit worn by the human actor to generate the time-varying positional data.

BACKGROUND OF THE INVENTION

With the recent increases in computation speed and power in computer graphics equipment, it has now become feasible to animate by computer a full-body, three-dimensional, cartoon character in real-time (24 to 30 frames per second) using real-time positional data from a human actor. In real-time computer animation, it is desirable to have the cartoon character (or virtual-reality character) move in relation to the motion of the human actor in a near instantaneous manner, which enables both the actor and the animation director to view and guide the animation results as the animation is being performed.

This type of computer animation requires between six to twenty (6–20) position and/or rotation sensors attached to selected parts of the human actor to adequately depict the motion of the character's head, torso, arms, hands, legs, and feet in relation to those of the human actor. Fewer sensors may be used when only some appendages of the character are to be animated (e.g., the upper body only for a ghost character), or when inverse kinematic calculations are used to estimate the motion of an appendage based on minimal number of sensors placed on the appendage. Fewer sensors may be needed when the animated character has fewer appendage joints than a human (such as a fish), and more sensors may be needed when the animated character has more joints (such as an insect). One prior art approach attaches reflective "dots" on the human actor and uses a number of cameras, set at different angles, to record the motion of all the dots. Two or more two-dimensional trajectories for each dot are thereby recorded by the cameras, and these two-dimensional trajectories are then analyzed by computer to find the three-dimensional trajectory for the dot. Unfortunately, this approach has a number of disadvantages, the primary one being that it is often impossible for the computer to reliably determine the trajectories of two dots which collide in one or more of the camera views. A human operator is required to aid the computer program in making the determination. This disadvantage makes it nearly impossible to use the reflective-dot system for real-time animation applications.

A more reliable approach is to employ electromagnetic sensors which output three-dimensional data, thereby avoiding the problem of having to determine a three-dimensional trajectory from two or more two-dimensional trajectories. One such electromagnetic sensor is the ULTRATRAK sensor (Polhemus Company, Colchester, Vt., USA), which is set in a magnetic field pattern, and provides X, Y, and Z position information with respect to a reference point in the magnetic field, and also provides $\theta_X$, $\theta_Y$ and $\theta_Z$, rotational information with respect to the reference point. Each sensor is packaged in a relatively small housing (3 cm×2.5 cm×1.5 cm), and has relatively thick (0.5 cm diameter) cable emanating from the housing to carry the data to the computer. When using full sensor data and not relying on kinematic computations, each arm appendage (which includes shoulder, arm, wrist, and hand) requires four (4) sensors, and each leg appendage (which includes hip, leg, ankle, and foot) requires four (4) sensors. When animating the upper body, a sensor will be needed for the chest, and a sensor will be needed for the head. Typically, a total of eighteen (18) sensors would be needed to animate a humanoid character.

For this approach to work, the cables from the sensors must be routed so that they do not unduly restrict the actor's motions, and do not entangle the actor. Also, each sensor has to be affixed to the actor as firmly as possible in order to prevent slippage between the sensor and the actor, and thus prevent errors between the motion of the actor and the motion of the animated character. But, on the other hand, the attachment of the sensors and routing of the cables must be comfortable to the human actor since he will be acting with the sensors for several hours at a time, usually 5 hours or more, under typical production conditions.

Through their experience in developing real-time computer animation to successfully operate in real-life production environments, the inventors have found that the following three additional requirements, which have not been recognized by the prior art, must be met:

(1) In order to easily accommodate a number of restroom breaks and dinner breaks for the actor throughout the production day, the sensors and cables must be quickly and easily removed and re-attached.

(2) Since an electromagnetic sensor can periodically break and malfunction (typically once every 10 production days), and since production costs are typically $2,000 per hour, the sensors and cables must be easy to replace to minimize downtime.

(3) There must be flexibility in the placement of the sensors in order to provide the best correspondence of motion between the human actor and the animated character. Conventional thought in the prior art is that the sensor placement is not important and that the computer can mathematically scale the sensor data to match the dimensions of the animated character. The inventors, however, have found that certain locations provide the best sensor data, and that the best locations often depend upon the particular morphology of the actor as well as that of the animated character. The inventors have found that, in real production environments, the morphologies of the actors vary widely, and that the morphologies of the animated characters vary widely. In order to be effective in a real production environment, the sensors must be able to easily adapt to fit different actor morphologies and character morphologies while providing the best data, while being comfortable to the actor, and while being in the most secure position.

As will be apparent to the reader, several of these requirements are conflicting with one another. The present invention is directed to addressing these conflicting requirements to enable real-time computer animation to operate in production environments.

SUMMARY OF THE INVENTION

Broadly stated, exemplary data-suits according to the present invention comprise one or more sheaths capable of fitting over and encircling respective human appendages, preferably in a substantially conformal manner, and one or more attachment strips sewn onto, or otherwise adhered to, each sheath along the longitudinal axis of the appendage. Each attachment strip has fastening means disposed on its exposed surface which is capable of having a sensor detachably attached to it at a plurality of locations along a substantial length of the attachment strip, thereby enabling great flexibility in positioning the sensor. Each sensor has a complementary fastening means on at least one of its surfaces.

In preferred embodiments of the present invention, the sheaths are implemented with a body-suit made of material which tightly fits around the torso and appendages of a human actor; the sheaths are thereby joined together to form one or two pieces (e.g., top jacket portion and bottom pants portion). Also in preferred embodiments of the present invention, the attachment strips comprise a VELCRO fastener of a first type (either male or female) and are adhered to selected portions of the body-suit, and the sensors preferably comprise patches of a VELCRO fastener of the second type (either female or male). Also in preferred embodiments, various cable guides for the sensor cables are provided which hold the sensor cables on the body suit, and out of the way of the actor.

In further preferred embodiments of the present invention, at least one sensor is mounted on the top surface of a substantially rigid substrate, and a fastening means, such as a VELCRO patch, is adhered to the bottom surface of the substrate. The substrate provides greater stability and reliable holding power.

These features and other preferred features of the present invention are described below in greater detail.

Accordingly, it is an object of the present invention to enable each sensor to be affixed to the actor as firmly as possible in order to prevent slippage between the sensor and the actor, and thus prevent errors between the motion of the actor and the motion of the animated character, but to make the sensor comfortable to wear.

It is another object of the present invention to enable the sensors and sensor cables to be quickly and easily removed and re-attached.

It is another object of the present invention to enable the sensors and sensor cables to be easy to replace so as to minimize production down time.

It is another object of the present invention to enable flexibility in the placement of the sensors in order to provide the best correspondence of motion between the human actor and the animated character.

It is another object of the present invention to enable the cables from the sensors to be routed so that they do not unduly restrict the actor's motions, and do not entangle the actor.

These and other objects of the present invention will become apparent to those skilled in the art from the following detailed description of the invention, the accompanying drawings, and the appended claims.

BRIEF DESCRIPTION OF THE DRAWINGS

FIGS. 1 and 2 are front perspective views of an exemplary body-suit according to the present invention;

FIG. 3 is a front perspective view of a first exemplary data-suit according to the present invention;

FIG. 4 is a back perspective view of the data-suit shown in FIG. 3;

FIG. 5 is an exploded, bottom perspective view of a first exemplary sensor assembly according to the present invention;

FIG. 6 is a top perspective view of a second exemplary sensor assembly according to the present invention;

FIG. 7 is a front perspective view of a second exemplary data-suit according to the present invention;

FIG. 8 is a back perspective view of the data-suit shown in FIG. 7;

FIG. 9 is a front perspective view of a cable clamp used in the exemplary data-suit of FIGS. 7 and 8 according to the present invention;

FIG. 10 is a top plan view of an exemplary wrapping band according to the present invention.

FIG. 11 is a top perspective view of an exemplary biceps harness cable guide according to the present invention;

FIG. 12 is a bottom perspective view of the exemplary cable guide shown by FIG. 11.

FIG. 13 is a top perspective view of an exemplary forearm harness cable guide according to the present invention;

FIG. 14 is a bottom perspective view of the exemplary cable guide shown by FIG. 13.

FIG. 15 is a top perspective view of an exemplary thigh harness cable guide according to the present invention;

FIG. 16 is a bottom perspective view of the exemplary cable guide shown by FIG. 15.

FIG. 17 is a top perspective view of an exemplary calf harness cable guide according to the present invention;

FIG. 18 is a bottom perspective view of the exemplary cable guide shown by FIG. 17; and FIG. 19 is a front perspective view of a data-suit according to the prior art.

DETAILED DESCRIPTION OF THE INVENTION

An exemplary data-suit according to the present invention comprises a body-suit made of material which tightly fits around the torso and appendages of a human actor, and a plurality of attachment strips, preferably comprising VELCRO, sewn along selected portions of the torso and appendages of the body-suit where positional sensors and cable guides may be attached. An exemplary data-suit further comprises six (6) or more sensors which are adapted to be attached and detached from the attachment strips. In those embodiments of the present invention where the sensors have their signals conveyed by cables, the data-suit further comprises a plurality of cable guides for routing the cables of the sensors to a common collection point. The cable guides preferably attach to the attachment strips. Each of these components of the data-suit will be described below in greater detail.

FIGS. 1–4 show various views of a first embodiment of a data-suit according to the present invention at reference number 100 in FIG. 3. Referring to FIGS. 1 and 2, the data-suit 100 comprises an underlying body-suit 10 having a top portion 20, a bottom portion 40, a pair of hand gloves 60, and a pair of slippers 80, each of which preferably comprises an elastic fabric that tightly, but comfortably, fits around respective portions of a human actor 1. Top portion 20 preferably comprises the form of a long-sleeve shirt or a thin, tight-fitting jacket, and fits around the arm appendages and the torso of actor 1. Bottom portion 40 preferably comprises the form of long-legged pants with a mid-torso section and shoulder straps (e.g., long-legged overalls), and fits around the legs, thighs, hips, and lower torso of actor 1 from the actor's lower chest area to the actor's ankles. Top portion 20 and bottom portion 40 are preferably made of LYCRA material, but other suitable elastic materials may be used. Gloves 60 snugly, but comfortably, fit the actor's hands, and slippers 80 snugly, but comfortably, fit the actor's feet. Gloves 60 may also comprise LYCRA material or other suitable materials conventionally used to construct gloves. Slippers 80 may comprise conventional ballet slippers (non toe-shoe type), or may comprise elastic or LYCRA socks (ankle height type), preferably with an elastic ankle band or ankle ties to anchor the sock to the foot. The elastic fabrics and materials used above are capable of stretching between virtually any pair of points on the fabric (or material) when a tensile force is applied along the distance between the points, and capable of increasing the distance between said points by at least 5% when a tensile force is applied, and preferably by at least 20%. The fabrics (and materials) preferably return to within 2% of the initial distance when the tensile force is removed, and preferably return to within 2% of the initial distance even after a tensile force causing 15% expansion is repeatedly applied several times (e.g., tens of times).

Each of the sleeves of top portion 20 and the legs of bottom portion 40 provides an elastic sheath of material which capable of fitting over and encircling a human appendage in a substantially conformal manner (i.e., such that it substantially conforms to the shape of the appendage). Each of these such sheaths has a longitudinal dimension along the length of the appendage to which it is fitted over.

The actor puts on bottom portion 40 before putting on top portion 20. Either or both portions 20 and 40 may comprise fasteners which attach one portion to the other. In preferred embodiments, two elastic bands, each being roughly 10 cm in length, are coupled between top portion 20 and bottom portion 40 at the front of the actor. Each elastic band has one of its ends attached to bottom portion 40 on either side of the groin, and one half of a buckle coupler attached to its other end. The other half of the buckle coupler is attached to top portion 20 at either side of the lower stomach area. Each band is latched in place by coupling the two halves of the buckle coupler together. The construction of the buckle coupler is convention in the art, and such buckle couplers are sold commercially by several companies. The male half of the buckle coupler has two latching prongs which interfit into respective socket-type recesses of the female half of the buckle coupler. There are tab releases on the latching prongs to enable the actor to push the prongs away from the socket recesses, thereby enabling the male half to be uncoupled from the female half. Other types of couplings and fasteners may be used, such as clamps, clips, buttons, velcro, hook and eye fasteners, ball and snap fasteners, and elastic cords, to name a few. The length of the band may also be adjustable. Because data-suit 100 usually operates within a magnetic environment, the couplers and fasteners are preferably non-magnetic to prevent interfering with the interaction between the magnetic field and the sensors.

Top portion 20 preferably opens down the front, to one side of the actor's sternum to enable the actor to easily insert his arms into the sleeves. The right and left flaps of the top portion 20 preferably overlap one another, and are fastened together with fasteners placed down the edges of the flaps. Plastic snap fasteners are preferably used, but other types of fasteners may be used, such as ball and snap fasteners, buttons, hook and eye fasteners, a zipper, and velcro, all preferably being non-magnetic.

To ensure a tight but comfortable fit, top portion 20 further comprises a cinching strap at the back side of top portion 20 to take-in any loose fabric material and thereby adjust the fit of top portion 20 to actor 1. The cinching strap is attached to two spots on the lower back of top portion 20, the spots being separated from one another by roughly 15 cm. The cinching strap draws the two spots together to take up any loose fabric. Preferably, the cinching strap comprises an elastic VELCRO strip of one type (either male or female) having one end attached to the fabric at one spot, and a patch of VELCRO of the other type (either female or male) attached to the second spot. The spots are drawn, or "cinched", together by securing the VELCRO strip to the VELCRO patch at a desired point along the length of the VELCRO strip. In place of a VELCRO strip, one may use a strip with other fasteners (such as snap fasteners) disposed along the length of the strip, and with a receiving fastener used in place of the VELCRO patch. Also, the cinching strap may comprise a band, which may be elastic, that has one of its ends attached to one spot on the fabric, and another end loop through an adjustment buckle (or clip), which in turn is attached to the other fabric spot. Additional cinching straps may be added to the body-suit, if needed.

Although it is currently preferred to have top portion 20 and bottom portion 40 separate from one another, it may be appreciated that these two portions may be attached to form a single piece suit. One advantage of having these portions separate from one another is that the actor can readily use the restroom without having to remove top portion 20, which may require re-setting the cinching strap.

Data-suit 100 further comprises a plurality of attachment strips 22, 24, 26, 42, 44, 46, 48, 50 and 52 sewn to, or otherwise attached to, selected areas of body-suit 10 which provide areas where sensors and cable guides may be detachably attached to body-suit 10. Referring to FIG. 1, attachment strip 22 is sewn onto top portion 20 along the exterior side of the right arm, preferably running from the actor's neck to his wrist, passing through the top side of his shoulder. Attachment strip 24 is sewn onto top portion 20 along the exterior side of the left arm in a similar manner. Attachment strip 26 is sewn onto top portion 20 along the actor's sternum, or breast bone, extending from the neck to the waist. Referring to FIG. 2, attachment strip 42 is sewn onto bottom portion 40 along the right hip area at the external side thereof, and attachment strip 44 is sewn on along the left hip area in a similar manner. Each of attachment strips 42 and 44 extends from a point below the crotch level to a point which is at the waist level, or just above. Attachment strips 46 and 48 are sewn onto bottom portion 40 along the right and left thighs, respectively, at the centers of the front sides of the thighs. Each of attachment strips 42 and 44 extend from a point just above the knee level to a point roughly even with the crotch level. Attachment strips 50 and 52 are sewn onto bottom portion 40 along the external sides of the right and left calves, respectively, and extend from a point a few centimeters below the knee level to the ankle level. Finally, attachment strips 82 and 84 are attached to the top surfaces of the right and left slippers 80, respectively, and extend from the ankle area to the beginning of the toe area.

In preferred embodiments of the present invention, the aforementioned attachment strips comprise female type VELCRO, and have a width of at least 3 cm, and preferably between 4 cm and 10 cm, with a width of 5 cm being typical. The length of each attachment strip should be chosen to extend along the sections indicated above. However, shorter sections may be used, and each of the longer attachment strips, such as attachment strip 22 or 24, may be implemented as a series of smaller attachment strips.

Gloves 60 comprise attachment patches 62 sewn, or otherwise adhered to, the top hand areas of the gloves. Patches 62 which provide areas where sensors may be attached to the actor's hands, and preferably comprise female VELCRO. The areas of patches 62 are preferably larger then the attachment areas of the sensors so that there is flexibility in positioning the sensors on gloves 60.

Referring now to FIG. 3, which shows a front perspective view of data-suit 100 as worn by actor 1, the attachment of sensors and cable guides to data-suit 100 will be described. Data-suit 100 comprises a plurality of sensors 122–126, 128 and 129 which are detachably attachable to attachment strips 22, 24 and 26 on top portion 20 of the body suit, as indicated in TABLE I.

TABLE I

| Sensor | Attachment Location |
|---|---|
| Right shoulder sensor 122 | Attached to strip 22, preferably near its upper end. |
| Left shoulder sensor 124 | Attached to strip 24, preferably near its upper end. |
| Right biceps sensor 123 | Attached to strip 22 at its mid-section, preferably just above the right elbow joint. |
| Left biceps sensor 125 | Attached to strip 24 at its mid-section, preferably just above the left elbow joint. |
| Chest sensor 126 | Attached to strip 26, preferably in its upper half. |
| Right hand sensor 128 | Attached to the top surface of the right hand, on a patch 62. |
| Left hand sensor 129 | Attached to the top surface of the left hand, on a patch 62. |

(The "left" and "right" designations provide in TABLE I, and all other tables herein, are made with respect to what actor 1 recognizes as being his "left" and "right" sides.) As described in greater detail below, each sensor is detachably mounted on a substrate (e.g., a disc), on the top surface thereof. A patch of male-type VELCRO is glued (preferably permanently) onto the bottom surface of the substrate, which is used to detachably attach each of the above sensors and its corresponding substrate to the location indicated in TABLE I.

In a similar manner, data-suit 100 comprises a plurality of sensors 142, 144, 146, and 148 which are detachably attachable to attachment strips 42, 44, 46, and 48, respectively, on bottom portion 40 of the body suit, as indicated in TABLE II. Data-suit 100 further comprises a sensor 182 attached to strip 82 on right slipper 80, and a sensor 184 attached to strip 84 on left slipper 80, as indicated in TABLE II.

TABLE II

| Sensor | Attachment Location |
|---|---|
| Right hip sensor 142 | Attached to strip 42. |
| Left hip sensor 144 | Attached to strip 44. |
| Right thigh sensor 146 | Attached to strip 46, preferably at the lower end of strip 46. |
| Left thigh sensor 148 | Attached to strip 48, preferably at the lower end of strip 48. |
| Right foot sensor 182 | Attached to strip 182, preferably at the midpoint of strip 182. |
| Left foot sensor 184 | Attached to strip 184, preferably at the midpoint of strip 184. |

Each of sensors 142, 144, 146, 148, 182 and 184 preferably comprises the above sensor-on-substrate construction. For the purpose of enabling flexibility of sensor placement, each of attachment strips 26, 42, 44, 46, 48, 50, and 52 should be at least 15 cm in length. Additionally, there should be a segment of attachment strip 22 in the biceps region of at least 10 cm in length, a segment of strip 22 in the forearm region of at least 10 cm in length, and a segment of attachment strip 22 in the shoulder region of at least 5 cm in length. These minimum lengths are applicable to strip 24 as well. These segments may be provided by individual attachment strips rather than by a single attachment strip.

Data-suit 100 further comprises two wrist sensors 130 and 132, a head sensor 134, and two ankle sensors 136 and 138, as indicated in TABLE III, with each being detachably attached to a corresponding wrap band, as indicated in the table

TABLE III

| Sensor | Attachment Location |
|---|---|
| Right wrist sensor 130 | Attached to a wrap band 70 which is detachably wrapped around the right wrist. |
| Left wrist sensor 132 | Attached to a wrap band 72 which is detachably wrapped around the right wrist. |
| Head sensor 134 | Attached to a wrap band 74 which is detachably wrapped around the right wrist. |
| Right ankle sensor 136 (Best seen in FIG. 4) | Attached to a wrap band 76 which is detachably wrapped around the right ankle. |
| Left ankle sensor 138 | Attached to a wrap band 78 which is detachably wrapped around the left ankle. |

Each of sensors 130, 132, 134, 136, and 138 preferably comprises the above sensor-on-substrate construction. The construction of bands 70, 72, 74, 76, and 78 is shown in greater detail by FIG. 10, where an exemplary band 700 is shown in a top plan view. Band 700 comprises a strip 702 of elastic material having a width of at least 3 cm and a length sufficient to wrap around a human appendage for which band 700 is to be used (e.g., head, wrist, or ankle). Elastic Band 702 is capable of stretching along its length when a tensile force is applied along its length, at its longitudinal ends. Band 702 is capable of increasing its length by at least 5% when a tensile force is so applied, and preferably by at least 20%; and is capable of returning to within 2% of its initial length when the tensile force is removed. Elastic band 702 is preferably capable of returning to within 2% of the initial distance even after a tensile force causing 15% expansion is repeatedly applied several times (e.g., tens of times).

Elastic band 700 further comprises a strip 703 of female-type VELCRO sewn, or otherwise adhered, to a place within the mid-portion of band 702. Patch 703 is used to receive and hold a sensor unit, as show in FIG. 10. Strip 703 preferably has a length longer than its width to enable the sensor to have several different attachment locations. Band 700 further comprises a strip 704 of male-type VELCRO which has a width which is approximately less than or equal to the width of the elastic strip 702, and a length which is less than the length of the elastic strip 702. Strip 704 is sewn or otherwise adhered to a surface of the elastic strip 702 at one end of strip 702, with the hooking ends of the male-type VELCRO faced outward from the surface of the elastic strip 702. Similarly, band 700 further comprises a strip 705 of female-type VELCRO which has a width which is approximately less than or equal to the width of the elastic strip 702, and a length which is less than the length of the elastic strip 702. Strip 705 is sewn or otherwise adhered to a surface of the elastic strip 702 at the other end of strip 702, opposite to strip 704. The two ends of elastic strip 702 are wrapped around the appropriate appendage such that the male-type VELCRO of strip 704 contacts and detachably adheres to the female-type VELCRO of strip 705.

To be used as a wrist band, band 700 preferably has a width of approximately 4.5 cm and a length of approximately 20 cm. The width in this application may vary between approximately 3 cm and 6 cm, and the length may vary between approximately 15 cm and 25 cm. The wrist bands may be attached to the sleeve ends of top portion 20, such as by sewing, or may be separate. To be used as a ankle band, band 700 preferably has a width of approximately 5 cm and a length of approximately 30 cm. The width in this application may vary between approximately 3 cm and 7 cm, and the length may vary between approximately 25 cm and 35 cm. To be used as a head band, band 700 preferably has a width of approximately 5 cm and a length of approximately 50 cm. The width in this application may vary between approximately 3 cm and 7 cm, and the length may vary between approximately 45 cm and 55 cm.

Referring back to FIGS. 3 and 4, each sensor may comprise a cable which conveys the positional information measured by the sensor. These cables are to be routed to a computer, or a wireless transmitter pack (preferably attached to actor 1) which transmits the sensor information to the computer by radio signals. In either case, the computer reads the positional information provided by the sensor signals and animates a character based on the positional data. The computer and its use of the positional information do not form a part of the present invention, and a description thereof is not needed for one of ordinary skill in the art to make, wear, or otherwise use the data-suits according to the present invention. Needless to say, the positional information provided by the sensors may be used in a wide variety of applications in addition to character animation, such as remote control of robotic arms and measurements of ranges of motion of human subjects for medical purposes. Regardless of the application, the computer reads the information from the sensors and uses the positional information as required by the application. The data-suits according to the present invention are not limited to any one application, and do not require to be operated in any one application area since the data-suits merely provide sensor information.

In data-suit 100, the sensor cables are held to selected ones of the attachment strips 22, 24, 26, 46, 48, 50, and 52 by a plurality of cable guides 222–226, 246, 248, 250 and 252 of male-type VELCRO, which detachably attach to the female-type VELCRO of the attachment strips. Each of these cable guides is identified in TABLE IV, along with an indication as to which strip it is attached to and which sensor cables it holds:

TABLE IV

| Cable Guide | Attachment Location |
| --- | --- |
| Right forearm cable guide 222 | Attached to strip 22, preferably at point on the right forearm just below the elbow joint; holds cables from sensors 128 and 130. |
| Left forearm cable guide 224 | Attached to strip 24, preferably at point on the right forearm just below the elbow joint; holds cables from sensors 129 and 132. |
| Right biceps cable guide 223 | Attached to strip 22, preferably at point on the right biceps just below the shoulder joint; holds cables from sensors 123, 128 and 130. |
| Left biceps cable guide 225 | Attached to strip 24, preferably at point on the left biceps just below the shoulder joint; holds cables from sensors 125, 129 and 132. |
| Chest cable guide 226 | Attached to strip 26, preferably at the upper end of strip 26; holds the cable |

TABLE IV-continued

| Cable Guide | Attachment Location |
| --- | --- |
| | from chest sensor 126. |
| Right thigh cable guide 246 | Attached to strip 46, preferably at the upper end of strip 46; holds cables from sensors 146, 136, and 182. |
| Left thigh cable guide 248 | Attached to strip 48, preferably at the upper end of strip 48; holds cables from sensors 148, 138, and 184. |
| Right calf cable guide 250 (Shown best in FIG. 4) | Attached to strip 50, preferably at the upper end of strip 50; holds cables from sensors 136 and 182. |
| Left calf cable guide 252 | Attached to strip 52, preferably at the upper end of strip 52; holds cables from sensors 138 and 184. |

Instead of being attached to an attachment strip as indicated above, the cable guide may be attached to a separate patch of VELCRO which is sewn onto, or otherwise adhered to, the body-suit.

To hold one or more cables to the cable guide, the cable(s) are laid against the VELCRO patch, and a strip of opposing VELCRO is placed over the cable(s), attaching to the VELCRO patch on either side of the cable(s) and even between the cables. The combination of the VELCRO strip and the VELCRO patch thereby encircle and hold the cable(s) to the VELCRO patch. This construction is illustrated with reference to left thigh cable guide 248, which comprises a VELCRO patch 249 which detachably attaches to attachment strip 48, and a smaller strip of VELCRO 247, which covers the cables from sensors 148,138, and 184, and which has one of its ends sewn onto one side of patch 249, and which is then laid over the cable(s) to sandwich them between VELCRO pieces 247 and 249. (Patch 249 has VELCRO on both sides, one side for attachment to piece 247, and the other side for attachment to attachment strip 48.)

Referring to FIG. 4, the sensor cables are routed to the back of actor 1 to four collection cable guides 230, 232, 234 and 236 disposed on the back of actor 1 (i.e., on the back of top portion 20). Collection cable guide 230 collects the sensor cables from the actor's left arm appendage and head, guide 232 collects the sensor cables from the actor's right arm appendage and chest, guide 234 collects the sensor cables from the actor's left leg appendage, and guide 236 collects the sensor cables from the actor's right leg appendage. Each of the cable guides 230, 232, 234 and 236 comprises a patch 237 of VELCRO (preferably male-type) which is attached to a corresponding patch 239 of VELCRO (preferably female-type) sewn onto, or otherwise adhered to, top portion 20 of the body-suit. As with previous cable guides, each cable is held to its patch 237 by a smaller strip of VELCRO 238 which has one of its ends sewn onto one side of patch 237, and which is then laid over the cable(s) to sandwich them between VELCRO pieces 237 and 238. (Patch 237 has VELCRO on both sides, one side for attachment to piece 238, and the other side for attachment to patch 239.)

The cables from collection cable guides 230, 232, 234, and 236 are collected together by a grand collection guide 260 so that all the cables may be bundled together as a single cable for easy and tangle-free routing to the computer or to a wireless transmitter unit. Grand guide 260 may comprise a VELCRO wrapping band which is sewn onto, or otherwise adhered to, top portion 20 of the body suit, and which has two ends with complementary fitting VELCRO. Instead of being sewn on to the body suit, grand guide 260 may be attached to a VELCRO patch which in turn is sewn onto, or otherwise adhered to, top portion 20. Other banding elements may be used, such as a band with a cinching buckle.

Referring now to FIG. 5, an exploded, bottom perspective view of an exemplary sensor-on-substrate assembly 300 is shown. The sensor is housed within a housing 302 and has a cable 306 emanating from it. The sensor housing 302 has a flange mounting plate 304 integrally formed with it, and two mounting apertures 305 are formed at selected edges of plate 304. Sensor housing 304 is mounted to a disc-shaped, non-magnetic substrate 308 by non-magnetic bolts 312 which pass through the apertures 305 of plate 304, and through a pair of corresponding apertures 309 formed in substrate 308. The bolts 312 screw onto respective nuts 314, which are also preferably non-magnetic, and thereby clamp sensor housing 302 to substrate 308. Bolts 312 and nuts 314 preferably comprise plastic, such as for example nylon, and substrate 308 preferably comprises a dielectric material, such as plastic. A circular VELCRO piece 310, preferably of male-type, is glued or otherwise adhered to the bottom surface of substrate 308. VELCRO piece 310 enables attachment of the sensor and substrate 308 to a desired attachment strip, as described above. VELCRO piece 310 has two apertures 311 whose locations correspond to the locations of apertures 309 of plate 304, and whose diameters are slightly larger than the diameters of apertures 309. The larger diameters enable apertures 311 to function as countersinks for the heads of bolts 312. The above construction enables a broken sensor to be readily removed by unscrewing bolts 312 from nuts 314 and replaced with an new sensor.

The inventors have found that several of the broken sensors have failed due to breaks in the cable wires near where the cable exits from the sensor housing. An improved sensor 350 which addresses this failure is shown in a top perspective view in FIG. 6. In assembly 350, the substrate is modified to have a tab portion along the edge near the point where cable 306 exits from housing 302. The modified substrate is indicated at reference number 308'. The piece of VELCRO may be similarly modified, as is shown at 310'. The tab portion enables a cable holding bracket 352 to be positioned near the exit point of cable 306 to clamp cable 306 to substrate 308' near the exit point. Bracket 352 is non-magnetic, and is affixed to substrate 308 by one or more non-magnetic bolts 356 and nuts 354. The inner side of bracket 352 may be padded with a flexible material, such as rubber or a cured silicone material, to minimize sharp angles in cable 306 near bracket 352 and pinching of cable 306 by bracket 352.

As can be seen, the above-described constructions of the sensors and cable guides enables these components to be readily attached and detached from the body-suit 10, thus enabling the actor to easily take dinner breaks and restroom breaks. Additionally, the sensor construction enables a broken or malfunctioning sensor to be readily replaced, thereby reducing down-time of the system. Additionally, the construction of the sensors and the long length of the attachment strips 22, 24, 26, 42, 44, 46, 48, 50, 52, 82, and 84 enable the position for each sensor to be found which provides the best data collection, the best secure adherence of the sensor to the actor, and the best comfort to the actor. The cable guides provide the following benefits:

(1) They segregate the cables to the various appendages into four basic groups to prevent the cables from becoming unduly tangled when the sensors and guides are removed from the actor. In this regard, a label may be affixed to each cable guide to indicate its position on the actor.

(2) The cable guides enable a controlled amount of slack in the cables between the sensor and the cable guide, and between adjacent cable guides. This enables the cables to readily move with the movements of the actor, but to not get in the actor's way or entangle the actor.

(3) The cable guides enable sensors and cables to be readily replaced as the cable may be easily slipped into and out of the holder formed by the VELCRO patch and fabric overlay (e.g., 247 and 248 shown in FIG. 3).

In the above illustrate embodiment, certain component comprise female-type VELCRO while other components comprise male-type VELCRO. It may be appreciated that the assignment of the VELCRO types may be reversed. It may also be appreciated that, in a broad view, the VELCRO of attachment strips 22, 24, 26, 42, 44, 46, 48, 50, 52, 82, 84, and 702 (and other attachment strips described below) comprises a first fastening means and the VELCRO of the sensors 122–126, 128–130, 132, 134, 136, 138, 142, 144, 146, 148, 182 and 184 comprises a second fastening means, and that these two fastening means interlock with one another to hold the components together. Typically, the male-type VELCRO is a hook-type fastener (having a plurality of hooks), and the female-type VELCRO is a loop-type fastener (having a plurality of loops which attach to the hooks of the male VELCRO). Moreover, it may be appreciated that the above fastening means may use different fasteners, such as rows of snap fasteners or rows of larger hooks and loops, although such other types of fasteners are currently not as preferred as the VELCRO fasteners.

The embodiment shown in FIGS. 3 and 4 is simple and adequate for applications where the motion of the character's appendages is relatively slow or moderate. For more aggressive motion capture applications, the data-suit shown at 400 in FIGS. 7–8 may be used. Data-suit 400 comprises body-suit 10 described above and shown in FIGS. 1 and 2, and comprises the previously described sensors 122–126, 128–130, 132, 134, 136, 138, 142, 144, 146, 148, 182 and 184 and wrap bands 70, 72, 74, 76, and 78, all substantially in the attachment locations previously described with respect to data-suit 100 shown in FIGS. 3 and 4. Data-suit 400 comprises a set of harness-type cable guides which are different from those of data-suit 100 and which enable the actor to perform more aggressive motions. Specifically, the harness cable guides route the sensor cables further toward the back of the actor, which keeps the cables more out of the way for the actor. Additionally, the harness cable guides are less prone to fall off of the attachments strips during vigorous motion.

The harness cable guides have the same general locations as the cable guides of data-suit 100, and are indicated by reference numbers 422–426, 446, 448, 450 and 452 in FIGS. 7 and 8. Briefly, each harness cable guide comprises a leather patch (preferably of moderate stiffness), a re-closeable band which encircles one of the actor's appendages and which is attached to the leather patch, and one or more re-closeable cable clamps attached to the outer surface of the leather patch. The cable clamps hold selected sensor cables to the leather patch, and may be readily opened and re-closed to facilitate the replacement of a broken sensor. To lock the harness to body-suit 10 and to stabilize it, the harness cable guide further comprises a patch of male-type VELCRO sewn to the harness (to either the band, the leather patch, or to both) which mates and adheres to one of attachment strips 22, 24, 26, 46, 48, 50 or 52 (female-type VELCRO) of body-suit 10. This patch of VELCRO is common to the cable guides of data-suit 100. The construction of the harness cable guides are shown and described in greater detail below. For the time being, each of these harness cable guides is identified in TABLE V, along with an indication as to which attachment strip it is attached to and which sensor cables it holds:

TABLE V

| Harness Cable Guide | Attachment Location |
| --- | --- |
| Right forearm cable guide 422 | Attached to strip 22, preferably at point on the right forearm just below the elbow joint; holds cables from sensors 128 and 130. |
| Left forearm cable guide 424 | Attached to strip 24, preferably at point on the right forearm just below the elbow joint; holds cables from sensors 129 and 132. |
| Right biceps cable guide 423 | Attached to strip 22, preferably at point on the right biceps just below the shoulder joint; holds cables from sensors 123, 128 and 130. |
| Left biceps cable guide 425 | Attached to strip 24, preferably at point on the left biceps just below the shoulder joint; holds cables from sensors 125, 129 and 132. |
| Right thigh cable guide 446 | Attached to strip 46, preferably at the upper end of strip 46; holds cables from sensors 146, 136, and 182. |
| Left thigh cable guide 448 | Attached to strip 48, preferably at the end of strip 48; holds cables from sensors 148, 138, and 184. |
| Right calf cable guide 450 (Shown best in FIG. 8) | Attached to strip 50, preferably at the upper end of strip 46; holds cables from sensors 136 and 182. |
| Left calf cable guide 452 (Shown best in FIG. 8) | Attached to strip 52, preferably at the upper end of strip 52; holds cables from sensors 138 and 184. |

Referring to FIG. 8, data-suit 400 further comprises an upper-back harness 480 and a waist harness 460 which collect the sensor cables from the appendages of the data-suit and routes the cables as a bundle to the computer or wireless transmitter pack. Upper-back harness 480 comprises a large leather patch 482, two re-closeable shoulder wrap bands 483 and 484, and a cross band 485 which connects between shoulder wrap bands 483 and 484 and crosses horizontally to the actor's chest, as best shown in FIG. 7. Shoulder wrap bands 483 and 484 are preferably elastic and have complementary VELCRO ends which provide a closure fastener. It may be appreciated that other closure fasteners may be used, such as snap fasteners, buttons, hook and eye fasteners, and buckle couplers, all preferably being non-magnetic. Referring to FIG. 7, cross band 485 has two pieces, each piece being sewn, adhered, or fastened to a respective shoulder band 483 and 484, and has a buckle coupler 486 which couples the two pieces together. The construction of the buckle coupler was previously described above, and such buckle couplers are sold commercially by several companies. Other types of couplings and fasteners may be used, such as snap fasteners, buttons, VELCRO, hook and eye fasteners, ball and snap fasteners, to name a few. The length of cross band 485 may also be adjustable such as by a cinching buckle. Because data-suit 400 usually operates within a magnetic environment, the couplers and fasteners are preferably non-magnetic to prevent interfering with the interaction between the magnetic field and the sensors.

A re-closeable cable clamp 487 is sewn or otherwise adhered to cross band 485 to hold and guide the cable from chest sensor 126. The construction of cable clamp 487 is shown in greater detail in FIG. 9 by an exemplary cable clamp 500, which is used for clamp 487 and other cable clamps on back harness 480. Cable clamp 500 comprises an attachment frame 502, which is used to adhere the clamp to an intended structure (such as cross band 485), an elongated piece 504 of compressible foam attached to the front side of attachment frame 502, and a swing arm 506 attached to frame 502 and positioned to close onto foam piece 504 or near foam piece 504. Arm 506 has a prong end 508 which interfits into a clip lock member 510, which in turn is attached to frame 502. Once prong end 508 is pushed into lock member 510, it remains there until member 510 is pushed outward by a force applied to a thumb tab 512 of member 510. The sensor cables run transverse to the lengths of arm 506 and foam piece 504, and are held between arm 506 and foam piece 504 when prong end 508 is latched to lock member 510. The shape of foam piece 504 is compressed to accommodate the cables, and the foam piece 504 provides a frictional holding force to the cable which minimizes or prevents slippage of the cable in the transverse direction. Arm 506 may be readily opened and closed so as to enable easy replacement of sensor cables associated with defective sensors. Frame 502 may comprise apertures 514 at its distal ends to facilitate attachment of clamp 500 to an intended structure by sewing or riveting. The back side of frame 502 may also be adhered to the intended structure, or a suitable VELCRO strip may be adhered to the back side of frame 502. A typical overall foot-print dimension for clamp 500 is 4.5 cm by 2 cm.

Referring back to FIG. 8, the sensor cables from cable guides 422–425, head sensor 134, and chest sensor 126 are routed to leather patch 482, and upper-back harness 480 comprises three cable clamps 488 affixed or adhered to leather patch 482 for collecting and holding these cables. Cable clamps 488 preferably have the same construction as cable clamp 500 shown in FIG. 9. From clamps 488, the sensor cables are bundled together by a VELCRO wrap band 490 before being routed down to waist harness 460. Wrap band 490 has two ends with complementary fitting VELCRO, and may be loose or attached to leather patch 482, such as by sewing or gluing.

Leather patch 482 preferably has a portion 489 of material which is cut out from the main piece of material. Cut-out portion 489 begins from the middle of the bottom side of patch 482 and extends upward to middle interior point of leather patch 482. Cut-out portion 489 enables the actor's shoulders to have full pivotal ranges of motion while keeping the cable clamps 488 and sensor cables in suitable positions.

Waist harness 460 comprises a large leather patch 462, and a re-closeable waist belt 464, as best shown in FIG. 7, which holds leather patch 462 to the actor. Belt 464 has two pieces, each being sewn or fastened to a respective left or right end of leather patch 462, and has a buckle coupler 466 which couples the two pieces together. The construction of the buckle coupler was previously described above, and such buckle couplers are sold commercially by several companies. Other types of couplings and fasteners may be used, such as snap fasteners, buttons, VELCRO, hook and eye fasteners, ball and snap fasteners, to name a few. The length of belt 464 may be adjustable, and may be elastic. Because data-suit 400 usually operates within a magnetic environment, the couplers and fasteners are preferably non-magnetic to prevent interfering with the interaction between the magnetic field and the sensors.

The sensor cables from harness cable guides 446, 448, 450, and 452 are routed to leather patch 462, and waist harness 460 comprises two cable clamps 468 affixed to leather patch 462 for collecting and holding these cables. Cable clamps 468 preferably have the same construction as cable clamp 500 shown in FIG. 9. From clamps 468, the sensor cables are bundled together by a VELCRO wrap band 470 before being routed to the computer or wireless transmitter pack. Wrap band 470 also collects the sensor cables from upper-back harness 480. Wrap band 470 has two ends with complementary fitting VELCRO, and may be loose or attached to leather patch 462, such as by sewing.

Leather patch 462 preferably has a portion 469 of material which is cut out from the main piece of material. Cut-out portion 469 begins from the middle of the bottom side of patch 462 and extends upward to middle interior point of leather patch 462. Cut-out portion 469 enable the actor's hips and buttocks to have full pivotal ranges of motion while keeping the cable clamps 468 and sensor cables in suitable positions.

Biceps Harness Cable Guide

FIG. 11 shows a front perspective view of biceps harness cable guide 423 (or 425) at 600, and FIG. 12 shows a back perspective view thereof. Biceps harness guide 600 comprises a diamond-shaped leather patch 602 having a long axis of about 15 cm and a short axis of about 11.5 cm. Two band pieces 604A and 604B, each approximately 3 cm wide, are attached to the opposing vertices of diamond patch 602 that lie on the short axis (11.5 cm). Band piece 604A is approximately 25 cm in length, and band piece 604B is approximately 10 cm in length. Two small patches 606A and 606B of complementary VELCRO are sewn, or otherwise adhered, to the distal ends of band pieces 604A and 604B, respectively, which enable band pieces 604A and 604B to wrap around the actor's biceps and attach to one another. For this purpose, VELCRO patch 606A is attached at the top surface of band piece 604A, whereas VELCRO patch 606B is attached at the bottom surface of band piece 604B. Band pieces 604A and 604B are preferably elastic to provide a comfortable attachment to actor 1.

Two cable clamps 500, which were previously described above, are attached to the top surface of patch 602, as shown in FIG. 11. The cable clamps 500 are roughly parallel to a common line (e.g., within 25° of one another), and are disposed near outer edges of the diamond-shaped patch 602. A sensor cable is shown passing through the two clamps 500.

Referring to FIG. 12, biceps harness guide 600 further comprises two patches 608A and 608B of male-type VELCRO, which are sewn or otherwise adhered to the proximal ends of band pieces 604A and 604B, respectively. Patches 608A and 608B, which may for example measure about 6 cm by about 3 cm, are also adhered to portions of leather patch 602 which are adjacent to the proximal ends of band pieces 604A and 604B, respectively. Patches 608A and 608B are typically adhered to these portions of leather patch 602 by and adhesive, but may be sewn. One or the other of patches 608A and 608B will be attached to the female type VELCRO of attachment strip 22 (or 24) when biceps harness guide 600 is coupled around the actor's biceps. With patches 608A and 608B being positioned to the sides of leather patch 602, harness 600 may be positioned to face more towards the back side of the actor rather than his front side, thereby enabling the cables to be routed away from the front space of the actor, where much of the actor's motion will occur. Patches 608A and 608B also stabilize and hold harness 600 to body-suit 10, thereby keeping it from falling off or slipping during vigorous motion.

Forearm Harness Cable Guide

FIG. 13 shows a front perspective view of forearm harness cable guide 422 (or 424) at 620, and FIG. 14 shows a back perspective view thereof. Forearm harness guide 620 comprises a diamond-shaped leather patch 622 having a long axis of about 12.5 cm and a short axis of about 10.5 cm. Two band pieces 624A and 624B, each approximately 3 cm wide, are attached to the opposing vertices of diamond patch 622 that lie on the long axis (12.5 cm). Band piece 624A is approximately 20 cm in length, and band piece 624B is approximately 10 cm in length. Two small patches 626A and 626B of complementary VELCRO are sewn, or otherwise adhered, to the distal ends of band pieces 624A and 624B, respectively, which enable band pieces 624A and 624B to wrap around the actor's forearm and attach to one another. For this purpose, VELCRO patch 626A is attached at the top surface of band piece 624A, whereas VELCRO patch 626B is attached at the bottom surface of band piece 624B. Band pieces 624A and 624B are preferably elastic to provide a comfortable attachment to actor 1.

Two cable clamps 500, which were previously described above, are attached to the top surface of patch 622, as shown in FIG. 13. The cable clamps 500 are disposed along the adjacent outer edges of the diamond-shaped patch 622, with their longitudinal axes being roughly perpendicular (i.e., between 45° and 135°). A sensor cable is shown passing through the two clamps 500.

Referring to FIG. 14, forearm harness guide 620 further comprises two patches 628A and 628B of male-type VELCRO, which are sewn or otherwise adhered to the proximal ends of band pieces 624A and 624B, respectively. Patches 628A and 628B, which may for example measure about 6 cm by about 3 cm, are also adhered to portions of leather patch 622 which are adjacent to the proximal ends of band pieces 624A and 624B, respectively. Patches 628A and 628B are typically adhered to these portions of leather patch 622 by adhesive, but may be sewn. One or the other of patches 628A and 628B will be attached to the female type VELCRO of attachment strip 22 (or 24) when forearm harness guide 620 is coupled around the actor's forearm. With patches 628A and 628B being positioned to the sides of leather patch 622, harness 620 may be positioned to face more towards the back side of the actor rather than his front side, thereby enabling the cables to be routed away from the front space of the actor, where much of the actor's motion will occur. Patches 628A and 628B also stabilize and hold harness 620 to body-suit 10, thereby keeping it from falling off or slipping during vigorous motion.

Thigh Harness cable guide

FIG. 15 shows a front perspective view of thigh harness cable guide 446 (or 448) at 640, and FIG. 16 shows a back perspective view thereof. Thigh harness guide 640 comprises a diamond-shaped leather patch 642 having a long axis of about 16.5 cm and a short axis of about 11.5 cm. Two band pieces 644A and 644B, each approximately 3 cm wide, are attached to the opposing vertices of diamond patch 642 that lie on the long axis (16.5 cm). Band piece 644A is approximately 40 cm in length, and band piece 644B is approximately 10 cm in length. Two small patches 646A and 646B of complementary VELCRO are sewn, or otherwise adhered, to the distal ends of band pieces 644A and 644B, respectively, which enable band pieces 644A and 644B to wrap around the actor's thigh and attach to one another. For this purpose, VELCRO patch 646A is attached at the top surface of band piece 644A, whereas VELCRO patch 646B is attached at the bottom surface of band piece 644B. Band pieces 644A and 644B are preferably elastic to provide a comfortable attachment to actor 1.

Two cable clamps 500, which were previously described above, are attached to the top surface of patch 642, as shown in FIG. 15. The cable clamps 500 are roughly parallel to a common line (e.g., within 25° of one another), and are disposed near outer edges of the diamond-shaped patch 642. A sensor cable is shown passing through the two clamps 500.

Referring to FIG. 16, thigh harness guide 640 further comprises two patches 648A and 648B of male-type VELCRO, which are sewn or otherwise adhered to the proximal ends of band pieces 644A and 644B, respectively. Patches 648A and 648B, which may for example measure about 6 cm by about 3 cm, are also adhered to portions of leather patch 642 which are adjacent to the proximal ends of band pieces 644A and 644B, respectively. Patches 648A and 648B are typically adhered to these portions of leather patch 642 by adhesive, but may be sewn. One or the other of patches 648A and 648B will be attached to the female type VELCRO of attachment strip 46 (or 48) when thigh harness guide 640 is coupled around the actor's thigh. With patches 648A and 648B being positioned to the sides of leather patch 642, harness 640 may be positioned to face more towards the back side of the actor rather than his front side, thereby enabling the cables to be routed away from the front space of the actor, where much of the actor's motion will occur. Patches 648A and 648B also stabilize and hold harness 640 to body-suit 10, thereby keeping it from falling off or slipping during vigorous motion.

Calf Harness Cable Guide

FIG. 17 shows a front perspective view of calf harness cable guide 450 (or 452) at 660, and FIG. 18 shows a back perspective view thereof. Calf harness guide 660 comprises a diamond-shaped leather patch 662 having a long axis of about 15.5 cm and a short axis of about 9.5 cm. Two band pieces 664A and 664B, each approximately 3 cm wide, are attached to the opposing vertices of diamond patch 662 that lie on the long axis (15.5 cm). Band piece 664A is approximately 30 cm in length, and band piece 664B is approximately 10 cm in length. Two small patches 666A and 666B of complementary VELCRO are sewn, or otherwise adhered, to the distal ends of band pieces 664A and 664B, respectively, which enable band pieces 664A and 664B to wrap around the actor's calf and attach to one another. For this purpose, VELCRO patch 666A is attached at the top surface of band piece 664A, whereas VELCRO patch 666B is attached at the bottom surface of band piece 664B. Band pieces 664A and 664B are preferably elastic to provide a comfortable attachment to actor 1.

Two cable clamps 500, which were previously described above, are attached to the top surface of patch 662, as shown in FIG. 17. The cable clamps 500 are disposed along the longer adjacent outer edges of the diamond-shaped patch 662, with their longitudinal axes being at an acute angle of between about 15° and 45°. A sensor cable is shown passing through the two clamps 500.

Referring to FIG. 18, calf harness guide 660 further comprises two patches 668A and 668B of male-type VELCRO, which are sewn or otherwise adhered to the proximal ends of band pieces 664A and 664B, respectively. Patches 668A and 668B, which may for example measure about 6 cm by about 3 cm, are also adhered to portions of leather patch 662 which are adjacent to the proximal ends of band pieces 664A and 664B, respectively. Patches 668A and 668B are typically adhered to these portions of leather patch 662 by adhesive, but may be sewn. One or the other of patches 668A and 668B will be attached to the female type VELCRO of attachment strip 50 (or 52) when calf harness guide 660 is coupled around the actor's calf. With patches 668A and 668B being positioned to the sides of leather patch 662, harness 660 may be positioned to face more towards the back side of the actor rather than his front side, thereby enabling the cables to be routed away from the front space of the actor, where much of the actor's motion will occur. Patches 668A and 668B also stabilize and hold harness 660 to body-suit 10, thereby keeping it from falling off or slipping during vigorous motion.

Each of band pieces 604A, 604B, 624A, 624B, 644A, 644B, 664A, 664B, preferably have widths about 3 cm, but may have widths as low as around 1.5 cm and as high as about 6 cm.

In the illustration of data-suit 400, certain components comprise female-type VELCRO while other components comprise male-type VELCRO. It may be appreciated that the assignment of the VELCRO types may be reversed. Moreover, it may be appreciated that strips and sensors may use different fasteners such as rows of snap fasteners, although such other types of fasteners are currently not as preferred as the VELCRO fasteners. It may also be appreciated that each of the above-described leather patches in all of the above-described cable harnesses may be implemented with a leather substitute, heavy rubberized fabric, or equivalents thereof.

FIG. 19 is a perspective view of a prior art data suit 900 which was developed by one or more of the inventors at MEDILAB Paris. A LYCRA shirt 902 was worn by the actor 1. Relatively flexible leather patches 904 were sewn to selected spots of shirt 902 or hand glove 60, and were designed to hold sensor units 950. Each leather patch 904 had crisscrossing elastic bands 906 which held the sensor units 950 to their respective patches 904. The leather patches 904 could not be re-positioned, and the sensors 950 could not be re-positioned. FIG. 19 only illustrates the sensors on the left side of data-suit 900; the right side is similarly constructed (but not illustrated).

The sensor cables were sewn into shirt 902 and emanated from the actor's back. The sensor cables were not generally bundled with the sensor cables from the right arm of the actor.

A terry-cloth headband 920, with VELCRO fastening means at the distal ends thereof (not shown), was placed around the actor's head. A female VELCRO patch 922 was sewn to the terry-cloth headband 920, and a sensor 950 (without a substrate) was attached thereto by a patch of male VELCRO.

While the present invention has been particularly described with respect to the illustrated embodiments, it will be appreciated that various alterations, modifications and adaptations may be made based on the present disclosure, and are intended to be within the scope of the present invention. While the invention has been described in connection with what is presently considered to be the most practical and preferred embodiments, it is to be understood that the present invention is not limited to the disclosed embodiments but, on the contrary, is intended to cover various modifications and equivalent arrangements included within the scope of the appended claims.

What is claimed is:

1. A sensor assembly capable of being detachably mounted to a human appendage, the sensor assembly comprising:

(a) a sheath of material which is capable of fitting over and encircling a human appendage such that it substantially conforms to the shape of the appendage, the sheath having an inside surface for contacting against the human appendage, an outside surface opposite to the inside surface, and a longitudinal dimension along the length of the appendage;

(b) a strip of hook and loop fastening material of a first type adhered to the outside surface of the sheath and having a width, and a length disposed along the longitudinal dimension of the sheath so that the length of the strip is disposed along the length of the human appendage when the sheath is fitted over and encircling the human appendage;

(c) a positional sensor contained within a housing, the housing having a first surface;

(d) a substrate having a first surface, a second surface, and a width across the substrate's second surface, the first surface of the housing for the positional sensor being attached to the substrate's first surface, the area of the substrate's first surface being greater than the area of the housing's first surface; and (e) a first piece of hook and loop fastening material of a second type adhered to the second surface of the substrate; and wherein the substrate is capable of being detachably mounted to the strip of hook and loop fastening material at its second surface at a plurality of points along the length of the hook and loop fastening material strip when the sheath is fitted over and encircling the human appendage with the first surface of the sheath contacting against the human appendage; and wherein the length of the strip is greater than the substrate's width.

2. The sensor assembly of claim 1 wherein the substrate comprises a disc.

3. The sensor assembly of claim 1 wherein the surfaces of the substrate are substantially flat.

4. The sensor assembly of claim 1 wherein the positional sensor comprises a wire cable extending from the housing, and wherein said sensor assembly further comprises a bracket which holds a portion of said wire cable to said substrate.

5. The sensor assembly of claim 4 wherein said substrate comprises a disc having a tab-shaped protrusion, and wherein said bracket is attached to said tab-shaped protrusion.

6. The sensor assembly of claim 1 wherein said strip of hook and loop fastening material has a width of at least 3 cm.

7. The sensor assembly of claim 6 wherein said strip of hook and loop fastening material has a length of at least 10 cm.

8. The sensor assembly of claim 1 wherein said strip of hook and loop fastening material has a length of at least 10 cm.

9. The sensor assembly of claim 1 wherein the positional sensor comprises a wire cable extending from the housing; and wherein the sensor assembly further comprises a second piece of hook and loop fastening material for attaching to a complimentary piece of hook and loop fastening material disposed on the sheath, the second piece of hook and loop fastening material comprising means for holding the wire cable of the sensor.

10. The sensor assembly of claim 9 wherein the second piece of hook and loop fastening material is of the second type, and wherein both the first and second pieces are attached to the strip of hook and loop fastening material.

11. The sensor assembly of claim 9 wherein the second piece of hook and loop fastening material comprises means for holding a second wire cable from a second positional sensor.

12. The sensor assembly of claim 1 wherein said sheath comprises an elastic material which is capable of stretching between a pair of points on the material when a tensile force is applied along the distance between the points, said elastic material capable of increasing the distance between said points by at least 20% when a tensile force is applied and thereafter returning to within 2% of the initial distance when the tensile force is removed.

13. The sensor assembly of claim 1 wherein said sheath comprises a body-fitting suit capable of covering at least two human appendages and at least a portion of a human torso.

14. A sensor assembly capable of being detachably mounted to a human appendage, the sensor assembly comprising:

(a) a sheath of material which is capable of fitting over and encircling a human appendage such that it substantially conforms to the shape of the appendage, the sheath having an inside surface for contacting against the human appendage, an outside surface opposite to the inside surface, and a longitudinal dimension along the length of the appendage;

(b) an attachment strip having a width of at least 3 cm and a length of at least 10 cm, the length being greater than the width, said strip being adhered to the outside surface of the sheath with its length disposed along the longitudinal dimension of the sheath so that the length of the strip is disposed along the length of the human appendage when the sheath is fitted over and encircling the human appendage, said attachment strip having a first fastening means disposed at a number of points along its length;

(c) a positional sensor contained within a housing, the housing having a first surface; and (d) a second fastening means coupled to said first surface and which is capable of interlocking with said first fastening means; and wherein the sensor is capable of being detachably mounted to the strip at a plurality of points along the length of said strip when the sheath is fitted over and encircling the human appendage with the first surface of the sheath contacting against the human appendage.

15. The sensor assembly of claim 14 wherein the positional sensor comprises a wire cable extending from the housing; and wherein the sensor assembly further comprises an attachment piece capable of attaching to said attachment strip disposed on the sheath, the attachment piece comprising means for holding the wire cable of the sensor.

16. The sensor assembly of claim 14 wherein said sheath comprises a body-fitting suit capable of covering at least two human appendages and at least a portion of a human torso.

17. The sensor assembly of claim 14 further comprising a substrate having a first surface and a second surface, the first surface of the housing for the positional sensor being attached to the substrate's first surface, the area of the substrate's first surface being greater than the area of the housing's first surface, and wherein said second fastening means is coupled to the substrate's second surface.

18. A sensor assembly capable of being detachably mounted to a human appendage, the sensor assembly comprising:

(a) an elastic band having an inside surface for contacting against a human appendage, an outside surface opposite to the inside surface, a width of at least 3 cm, and length sufficient to wrap around the human appendage, the elastic band capable of stretching along its length when a tensile force is applied along its length and at its longitudinal ends, the elastic band capable of increasing its length by at least 5% when a tensile force is applied and thereafter returning to within 2% of its initial length when the tensile force is removed;

(b) an attachment strip having a first surface, a second surface opposite to the first surface, a width which is approximately less than or equal to the width of the elastic band, and a length which is less than the length of the elastic band, the first surface of the attachment strip being adhered to the outside surface of the elastic band and the second surface of the attachment strip having a first fastening means disposed thereon;

(c) a positional sensor contained within a housing, the housing having a first surface;

(d) a substrate having a first surface, a second surface, and a width across the substrate's second surface, the first surface of the housing for the positional sensor being attached to the substrate's first surface, the area of the substrate's first surface being greater than the area of the housing's first surface, the bottom surface of said substrate comprising a second fastening means which is capable of interlocking with said first fastening means such that the substrate is capable of being detachable mounted to the outside surface of the elastic band, and wherein the width of the attachment strip is greater than the width of the substrate.

19. The sensor assembly of claim 18 wherein said elastic band comprises fastening means at its distal ends.

20. A sensor assembly capable of being detachably mounted to the thighs and hips of a human, the sensor assembly comprising:

a lower-body suit capable of fitting over and encircling the left and right thighs and the left and right hips of a human such that it substantially conforms to the shape of the thighs and hips of the torso, the lower-body suit having an inside surface for contacting against the human and an outside surface opposite to the inside surface;

a first attachment strip of a first type of hook and loop fastening material having a width and a length greater than the width, the first attachment strip being adhered to the outside surface of the lower-body suit such that the length of the first attachment strip is disposed along the length of the left thigh when the lower-body suit is worn on a human;

a second attachment strip of a first type of hook and loop fastening material having a width and a length greater than the width, the second attachment strip being adhered to the outside surface of the lower-body suit such that the length of the second attachment strip is disposed along the length of the right thigh when the lower-body suit is worn on a human;

a third attachment strip of a first type of hook and loop fastening material adhered to the outside surface of the lower-body suit such that the third attachment strip is disposed at the left hip of a human when the lower-body suit is worn on a human;

a fourth attachment strip of a first type of hook and loop fastening material adhered to the outside surface of the lower-body suit such that the fourth attachment strip is disposed at the right hip of a human when the lower-body suit is worn on a human; and a first positional sensor, a second positional sensor, a third positional sensor, and a fourth positional sensor, each positional sensor being contained within a respective housing, each respective housing having a first surface and a piece of a second type of hook and loop fastening material coupled to the housing's first surface and capable of interlocking with an attachment strip of a first type of hook and loop fastening material; and wherein the first and second positional sensors are capable of being detachably mounted to the first and second attachment strips, respectively, at a plurality of points along the length of each corresponding attachment strip.

21. The sensor assembly of claim 20 wherein the first positional sensor comprises a wire cable extending from the housing containing the sensor; and wherein the sensor assembly further comprises an additional piece of hook and loop fastening material for attaching to a complimentary piece of hook and loop fastening material disposed on the lower-body suit, the second piece of hook and loop fastening material comprising means for holding the wire cable of the first positional sensor.

22. The sensor assembly of claim 20 further comprising a first substrate having a first surface and a second surface, the first surface of the housing for the first positional sensor being attached to the first substrate's first surface, the area of the first substrate's first surface being greater than the area first surface of the housing for the first sensor's, and wherein the piece of a second type of hook and loop fastening material for the first sensor is adhere to the first substrate's second surface.

* * * * *